United States Patent
Tateno et al.

(10) Patent No.: US 9,643,918 B2
(45) Date of Patent: May 9, 2017

(54) CALCINATION APPARATUS, PROCESS FOR PRODUCING OXIDE CATALYST, AND PROCESS FOR PRODUCING UNSATURATED ACID OR UNSATURATED NITRILE

(71) Applicant: ASAHI KASEI CHEMICALS CORPORATION, Tokyo (JP)

(72) Inventors: Eri Tateno, Tokyo (JP); Masatoshi Kaneta, Tokyo (JP); Toshihiko Fukuzono, Tokyo (JP); Haruhiko Watanabe, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 34 days.

(21) Appl. No.: 14/874,140

(22) Filed: Oct. 2, 2015

(65) Prior Publication Data

US 2016/0023994 A1    Jan. 28, 2016

Related U.S. Application Data

(62) Division of application No. 13/985,952, filed as application No. PCT/JP2012/053157 on Feb. 10, 2012, now Pat. No. 9,180,427.

(30) Foreign Application Priority Data

Feb. 18, 2011   (JP) .................. 2011-033777

(51) Int. Cl.
| | |
|---|---|
| *B01J 23/28* | (2006.01) |
| *F27B 7/24* | (2006.01) |
| *C07C 253/24* | (2006.01) |
| *B01J 6/00* | (2006.01) |
| *B01J 19/24* | (2006.01) |
| *F27D 99/00* | (2010.01) |

(52) U.S. Cl.
CPC ............. *C07C 253/24* (2013.01); *B01J 6/004* (2013.01); *B01J 19/2415* (2013.01); *B01J 23/28* (2013.01); *F27B 7/24* (2013.01); *F27D 99/0073* (2013.01); *B01J 2219/00157* (2013.01); *B01J 2219/00162* (2013.01); *B01J 2219/24* (2013.01); *B01J 2523/00* (2013.01)

(58) Field of Classification Search
CPC .................................................... B01J 19/2415
See application file for complete search history.

(56) References Cited

U.S. PATENT DOCUMENTS

| | | | |
|---|---|---|---|
| 4,279,207 A * | 7/1981 | Wormser | F22B 31/0007 110/345 |
| 4,533,319 A | 8/1985 | Mathews et al. | |
| 5,227,105 A * | 7/1993 | Eucker | B28B 3/20 264/102 |
| 8,772,195 B2 | 7/2014 | Ishii et al. | |
| 2008/0014342 A1* | 1/2008 | Jakobi | B01J 19/0053 427/181 |
| 2009/0042723 A1 | 2/2009 | Wang et al. | |
| 2010/0286432 A1 | 11/2010 | Tateno et al. | |
| 2013/0253217 A1 | 9/2013 | Ishii et al. | |
| 2013/0274500 A1 | 10/2013 | Tamura et al. | |
| 2013/0310593 A1 | 11/2013 | Ishii et al. | |
| 2014/0024861 A1 | 1/2014 | Okumura et al. | |

FOREIGN PATENT DOCUMENTS

| | | |
|---|---|---|
| CN | 101117661 A | 2/2008 |
| JP | 59-119176 A | 7/1984 |
| JP | 2000-249476 A | 9/2000 |
| JP | 2001-133157 A | 5/2001 |
| JP | 2009-262146 A | 11/2009 |

OTHER PUBLICATIONS

International Search Report Issued in PCT/JP2012/053157, mailed on Apr. 24, 2012.

* cited by examiner

*Primary Examiner* — Nyeemah A Grazier
(74) *Attorney, Agent, or Firm* — Birch, Stewart, Kolasch & Birch, LLP

(57) ABSTRACT

Disclosed is a calcination apparatus, including: a calcination tube having open ends at both terminals; a pair of hoods, each hood covering each open end of the calcination tube; and a pair of rings, each ring sealing a gap between the calcination tube and the hood, wherein the rings are directly or indirectly fixed on an outer surface of the calcination tube; a groove is provided along a circumferential direction of the ring at a contact surface side between the ring and the hood; a sealed chamber surrounded by the hood and the groove is formed; and both the calcination tube and the rings rotate in a circumferential direction of the calcination tube while keeping the hood in contact with both sides of the groove.

16 Claims, 8 Drawing Sheets

CALCINATION APPARATUS, PROCESS FOR PRODUCING OXIDE CATALYST, AND PROCESS FOR PRODUCING UNSATURATED ACID OR UNSATURATED NITRILE

CROSS-REFERENCE TO RELATED APPLICATIONS

This application is a Divisional of co-pending application Ser. No. 13/985,952 filed on Aug. 16, 2013, which is a National Phase of PCT International Application No. PCT/JP2012/053157 filed on Feb. 10, 2012, which claims priority under 35 U.S.C. §119(a) to Patent Application No. 2011-033777 filed in Japan on Feb. 18, 2011. All of the above applications are hereby expressly incorporated by reference into the present application.

TECHNICAL FIELD

The present invention relates to calcination apparatuses, processes for producing an oxide catalyst, and processes for producing an unsaturated acid or an unsaturated nitrile.

BACKGROUND ART

Previously, processes for producing corresponding unsaturated nitrile by gas phase catalytic ammoxidation of propylene have been well known. However, a process has recently drawn attention, the process in which corresponding unsaturated nitrile is produced by gas phase catalytic ammoxidation using propane as a substitute for propylene. A large number of catalysts used have been proposed.

Patent Literature 1 discloses an ammoxidation catalyst for propane as a feedstock, the catalyst containing Mo, V, and Nb. With regard to this catalyst, it has been known that a calcination atmosphere is preferably kept under an inert gas atmosphere during a step of subjecting a catalyst precursor to calcination in view of catalytic performance.

CITED LIST

Patent Document 1: Japanese Patent Application Laid-Open No. 2009-262146

SUMMARY OF INVENTION

Technical Problem

In order to prepare a high-performance catalyst by uniformly calcinating a precursor at a predetermined temperature, it is preferable to heat the precursor while rotating a calcination crucible which has been kept under an inert atmosphere.

The present inventors have actually carried out continuous calcination by using a rotary kiln. Unfortunately, the present inventors have found that: although brief calcination has enabled the inside of the kiln to be kept under an inert gas atmosphere, due in part to deterioration of a sealed portion by rotation of the kiln, etc., long-term operation has caused air to infiltrate into a calcination tube and an inert gas atmosphere has been unable to be maintained. This has resulted in decreased catalytic performance.

In view of the above situation, it is an object of the present invention to provide a calcination apparatus which can maintain an atmosphere in a calcination tube even for long-term operation, a process for continuously producing a catalyst which produces an increased yield of a product of interest by using the calcination apparatus, and a process for producing an unsaturated acid or an unsaturated nitrile by using the catalyst obtained by the foregoing production process.

Solution to Problem

The present inventors have conducted intensive research to solve the above problem, and have found that an inert gas atmosphere inside a calcination tube can be maintained while preventing a sealing structure from wearing, by: covering both terminals of a calcination tube with hoods; sealing a gap between the calcination tube and the hood by using a ring to provide a structure in which air infiltration into the hood and the calcination tube and a gas leak from the calcination tube can be prevented; having a groove-like space in the ring, which space is open to the hood, to result in creating an additional space between the outside of the ring and the hood; and preferably supplying inert gas to the space as well. Then, the present inventors have completed the present invention.

Specifically, the present invention is described as follows.

[1] A calcination apparatus, including: a calcination tube having open ends at both terminals; a pair of hoods, each hood covering each open end of the calcination tube; and a pair of rings, each ring sealing a gap between the calcination tube and the hood,
wherein the rings are directly or indirectly fixed on an outer surface of the calcination tube;
a groove is provided along a circumferential direction of the ring at a contact surface side between the ring and the hood;
a sealed chamber surrounded by the hood and the groove is formed; and both the calcination tube and the rings rotate in a circumferential direction of the calcination tube while keeping the hood in contact with both sides of the groove.

[2] The calcination apparatus according to [1], further including a pair of flanges, each flange protruding from an inner surface of the hood toward an inside in a circumferential direction of the calcination tube, wherein each of the both sides of the groove is in contact with each of the pair of flanges.

[3] A calcination apparatus, including: a calcination tube having open ends at both terminals; a pair of hoods, each hood covering each open end of the calcination tube; and a pair of rings, each ring sealing a gap between the calcination tube and the hood,
wherein the rings are directly or indirectly fixed on an outer surface of the calcination tube;
each of the rings includes a plurality of annular members disposed in a width direction of the ring;
each of the plurality of annular members comes into contact with the hood;
a sealed chamber surrounded by at least the hood and the plurality of annular members is formed; and
both the calcination tube and the rings rotate in a circumferential direction of the calcination tube while keeping the hood in contact with the plurality of annular members.

[4] The calcination apparatus according to [3], further including a pair of flanges, each flange protruding from an inner surface of the hood toward an inside in a circumferential direction of the calcination tube, wherein each of the plurality of annular members is in contact with each of the pair of flanges.

[5] The calcination apparatus according to any one of [1] to [4], wherein a space surrounded by at least the calcination tube, the rings, and the hood is maintained under an inert gas atmosphere; and the sealed chamber is filled with an inert gas.

[6] The calcination apparatus according to [5], wherein the hood has a supply port for supplying the inert gas to the sealed chamber.

[7] The calcination apparatus according to [5] or [6], wherein an atmospheric pressure within the space is higher than an atmospheric pressure outside the space.

[8] The calcination apparatus according to any one of [5] to [7], wherein a pressure difference P1 represented by the following equation (1) is more than 0 mm $H_2O$ and 900 mm $H_2O$ or less:

$P1$=(an atmospheric pressure within the space)−(an atmospheric pressure outside the space) (1).

[9] The calcination apparatus according to any one of [5] to [8], wherein a pressure difference P2 represented by the following equation (2) is more than 0 mm $H_2O$ and 500 mm $H_2O$ or less:

$P2$=(a pressure of the sealed chamber)−(a pressure within the space) (2).

[10] The calcination apparatus according to any one of [5] to [9], wherein an oxygen concentration of the space is 1000 ppm or less.

[11] The calcination apparatus according to any one of [1] to [10], further including a unit for imparting an impact to the calcination tube.

[12] A process for producing an oxide catalyst, the process including the steps of:
feeding a catalyst precursor containing Mo, V, Nb, and Te and/or Sb from a first end of a calcination tube of the calcination apparatus according to any one of [1] to [11]; calcining the catalyst precursor in the calcination tube to yield a calcination product; causing the catalyst precursor and/or the calcination product to pass through a space surrounded by the calcination tube, a hood, and a ring; and discharging the calcination product from the space.

[13] The process for producing an oxide catalyst according to [12], wherein a calcination temperature during the step of calcining the catalyst precursor is set to a melting point or higher of an oxide of at least one metal element among metal elements included in the oxide catalyst and/or the catalyst precursor;
the process further includes the step of imparting an impact to the calcination tube while f represented by the following equation (3) satisfies $0.08 \leq f \leq 50$:

$f$=(vibration acceleration)/$C$ (3), wherein the vibration acceleration refers to vibration acceleration (m/s$^2$) of the impact imparted to the calcination tube; and C denotes a total mass (unit: % by mass) of the at least one metal element based on overall mass of the oxide catalyst.

[14] The process for producing the oxide catalyst according to [13], wherein the impact is imparted while f satisfies $0.1 \leq f \leq 40$.

[15] A process for producing an unsaturated acid or an unsaturated nitrile, the process including the step of: bringing an alkane or an alkene into contact with an oxide catalyst prepared using the process according to any one of [12] to [14] to carry out a gas phase catalytic oxidation reaction or a gas phase catalytic ammoxidation reaction to yield corresponding unsaturated acid or unsaturated nitrile.

Advantageous Effects of Invention

According to a calcination apparatus of the present invention, it can provide a calcination apparatus which can maintain an atmosphere in a calcination tube even for long-term operation, a process for continuously producing a catalyst which produces an increased yield of a product of interest by using the calcination apparatus, and a process for producing an unsaturated acid or an unsaturated nitrile by using the catalyst obtained by the foregoing production process.

DESCRIPTION OF EMBODIMENTS

Figure 1:
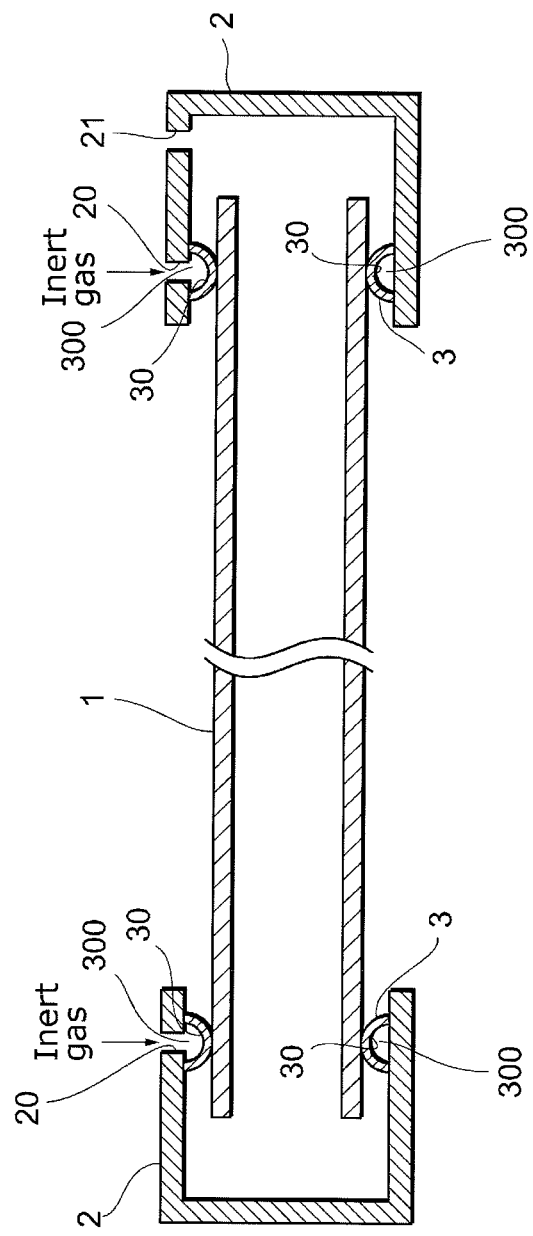
FIG. 1 is a schematic cross-sectional diagram briefly showing one example of a calcination apparatus according to the present embodiment.

Hereinafter, modes for carrying out the present invention (hereinafter, referred to as an embodiment of the present invention) will be specifically described by referring to Drawings depending on the need. In the Drawings, identical elements have identical reference numerals to avoid overlapping descriptions. In addition, relative positions such as the upper, lower, left, and right are based on the relative positions depicted in the Drawings, unless otherwise specified. Further, the size ratio of the Drawings is not limited to the ratio indicated in the Drawings. Moreover, the present invention is not limited to the following embodiments, and various modifications can be employed within the scope of its purport.

[Calcination Apparatus]

FIG. 1 is a schematic cross-sectional view schematically illustrating a calcination apparatus of an embodiment of the present invention as an example. This calcination apparatus includes a calcination tube 1 having open ends at both terminals and a pair of hoods 2 covering each of both the open ends of the calcination tube 1. As used herein, the phrase "the hood 2 covering each open end of the calcination tube 1" means that as demonstrated in FIG. 1 and FIGS. 2, 4, 5, and 7 to 9 below, the open end is covered so as not to cause the hood 2 to directly contact with an edge face of the open end of the calcination tube 1. A trunk of the calcination tube 1 is equipped with a heater (not shown). A feedstock is calcined while the feedstock fed by the first end flows and reaches the second end. The calcination tube 1 rotates in a circumferential direction by using a longitudinal axis, which enables heat to be uniformly distributed.

The calcination tube 1 may be horizontally held. When powder is subjected to continuous calcination and passes through from the first end of the calcination tube 1 to the second end, the calcination tube 1 may be installed for the longitudinal direction to form a predetermined angle with the horizontal direction so as to place the first end position higher than the second end position. Although the angle to hold the calcination tube 1 depends on the shape of a calcination product, etc., the angle is preferably from 0 to 70 degrees and more preferably from 0.1 to 20 degrees.

The wall thickness of the calcination tube 1 is not particularly limited so long as the thickness has a length sufficient to cause no damage by an impact described below. However, in view of its durability, the thickness is preferably 2 mm or more and more preferably 4 mm or more. In addition, from the viewpoint of sufficiently delivering an impact to the inside of the calcination tube 1, the wall thickness is preferably 100 mm or less and more preferably 50 mm or less. A material of the calcination tube 1 is not particularly limited if the material has heat resistance and strength that does not cause damage by the impact. For example, SUS can be preferably used. In the case of generation of corrosive gas during calcination, a material having heat resistance, impact resistance, and corrosion resistance can be preferably used as a material for the calcination tube. Examples of the material which can be preferably used include SUS304 and SUS310S. Any shape can be allowed if the calcination tube 1 is tubular. The cross-sectional shape perpendicular to its longitudinal direction is not limited. However, a cylinderical shape is preferable in view of availability and easy-to-maintain sealing characteristics of a rotating part.

A suitable size and material, etc., of the calcination tube 1 can be selected depending on types of calcination subjects, calcination conditions, or production volumes. However, in the case of a calcination apparatus which produces an oxide catalyst as described below, the inner diameter is preferably 70 to 2000 mm and more preferably 100 to 1200 mm, and the length is preferably 200 to 10000 mm and more preferably 800 to 8000 mm.

In order to be able to cover a terminal of the calcination tube 1, the hood 2 has an inner diameter larger than an outer diameter of the calcination tube 1. In addition, a ring 3 of an annular member is fitted to a gap between the hood 2 and the calcination tube 1. This ring 3 seals the gap between the calcination tube 1 and the hood 2. In order to maintain an atmosphere in the gap between the hood 2 and the calcination tube 1, it is preferable to fill the gap between the hood 2 and the ring 3 with inert gas in the case where the calcination tube 1 has an eccentric pivot, the position of the calcination tube 1 is instantaneously changed by a below-described impact on the calcination tube 1, or heat causes the calcination tube 1 to expand or contract parallelly and/or perpendicularly to an axis in a longitudinal direction. The inner diameter of the hood 2 is set to be larger than a total of the outer diameter of the calcination tube 1 and a length twice the thickness of the ring 3. This is preferable in view of keeping airtightness when the hood 2 moves toward the calcination tube 1 in a perpendicular and/or parallel direction to a rotation axis of the calcination tube 1, or the calcination tube 1 and/or the hood 2 expands or contracts. When the inner diameter of the hood 2 fits within the above preferable length, it is preferable to have a length 0 to 500 mm larger than a total of the outer diameter of the calcination tube 1 and a length twice the thickness of the ring 3, and it is more preferable to have a length 1 to 300 mm larger than the total. The space is sealed by the ring 3 to keep an atmosphere inside the hood 2. In view of this, the hood 2 preferably has a shape similar to that of the terminal of the calcination tube 1. For example, if the calcination tube 1 is cylinderical, the hood 2 is also preferably cylindrical.

In order to keep an space surrounded by the calcination tube 1, hood 2, and ring 3 and a sealed chamber 300 (specifically described below) formed between the hood 2 and the ring 3 under an inert gas atmosphere, the hood 2 is provided with an inert gas inlet 21 that is a supply port to feed inert gas to the above space, and is also provided with an inert gas inlet 20 that is a supply port to feed inert gas to the sealed chamber 300. As used herein, the phrase "space surrounded by a calcination tube, hood, and ring" (hereinafter, simply referred to as a "specific space") refers to inclusion of the inside of the calcination tube. The position of the inert gas inlet 21 is not particularly limited. However, it is preferable to provide the inert gas inlet 21 at such a position that the specific space can be sufficiently replaced and/or filled with inert gas. When the shape, size, and calcination subject of the calcination tube 1 are taken into consideration, the position, number, size, and inert gas flow volume of the inert gas inlet 21 can be suitably adjusted.

The inert gas inlet 21 is preferably installed in such a position as to prevent powder contamination on the contact surface between the ring 3 and the hood 2, or the inlet is preferably installed at a vicinity of the contact surface to prevent the contamination, which causes a gas flow to prevent the powder contamination. In order to prevent the powder contamination, an inert gas inlet 26 as described below may be additionally provided as a substitute for or in addition to the inert gas inlet 21. The inert gas inlet 21 may keep the specific space under an inert gas atmosphere and may prevent the above powder contamination. Depending on the size, structure, and required inert gas volume, etc., of the calcination apparatus, whether or not the inert gas inlets 21 and 26 are installed can be appropriately selected. However, from the viewpoint of making inert gas certainly circulate in the specific space, each of the inert gas inlets 21 and 26 is preferably installed.

In order to maintain the inside of the above specific space under an inert gas atmosphere, it is preferable to circulate inert gas when a tiny amount of air contaminated from the outside of the specific space and gas generated in the calcination tube 1 during calcination are taken into account. Accordingly, the hood 2 is preferably provided with a gas outlet (not shown), or the inert gas inlet 21 may be doubled as the gas outlet. A single or a plurality of the gas outlets may be allowed. The gas outlets may be each installed on the hood 2 at both the terminals or at either terminal. It is preferable to suitably adjust the position, number, and size of the gas outlet by taking into consideration the shape, size, and calcination subject of the calcination tube 1 in view of the following aspects: air contamination due to reflux of ambient air can be reduced; gas inside the specific space can be exhausted at a sufficient rate; a gas flow can be created in such a manner as to enable all the regions of the specific space to be uniformly replaced with inert gas; and others. The relative position regarding the inlet and the outlet is not particularly limited. However, from the viewpoint of making inert gas circulate, in the case of there being only one outlet, it is preferable to install the outlet at the opposite side of the surface having an inlet (i.e., the surface perpendicular to the longitudinal direction of the calcination tube 1). In addition, depending on the need, the gas inlet and/or outlet may have such a shape that a nozzle protrudes into the calcination tube 1 and/or the hood 2. The nozzle length can be adjusted so as to achieve a preferable tip position of the protruded nozzle in the case of giving calcination conditions an influence. This is because there are position-dependent changes in a gas flow in the specific space so that the components and concentrations of inert gas in the specific space and gas generated during calcination, etc., are going to be altered and the temperature distribution in the calcination tube 1 is going to be altered. The same applies to the nozzle length when the components such as gas generated at the specific location of the calcination tube 1 during calcination are intended to be selectively removed. The gas exhausted from the outlet may be contaminated with powder injected into the calcination tube. Accordingly, an exit port of the gas flow from the outlet can be provided with a gas-solid separator such as a cyclone. The powder separated by the gas-solid separator can be separately collected, or can be reintroduced into the calcination tube 1. In addition, depending on the need, in order to be able to select whether the powder is separately collected or is reintroduced into the calcination tube, a three-way valve or the like may be installed.

A nozzle can be installed so as to analyze gas components in the above specific space. This nozzle enables toxic gas to be detected in the case of there being a possibility of generating the toxic gas in the specific space, and also can determine a concentration of oxygen contaminated in the specific space due to some reason. The inert gas inlet 21 and/or the outlet may play this function as well.

A material of the hood 2 is not particularly limited. However, the material preferably has sufficient strength, heat resistance, and corrosion resistance in a manner similar to those of the calcination tube 1, and SUS is particularly preferable. The wall thickness of the hood is not particularly limited so long as it allows for sufficient strength, but in general, is preferably 0.1 to 500 mm and more preferably 0.2 to 100 mm.

The hood 2 can be equipped with a heating unit when a calcination subject and components such as gas and liquid generated during calcination are taken into consideration. For example, water and gas such as ammonia is generated in the calcination tube 1 during calcination; and these substances form powder and a mass on a wall surface or in an exhaust nozzle. This is because they condense by cooling in the exhaust nozzle and/or the hood 2 which is not heated due to their presence outside a heater, thereby inhibiting a flow of the powder and/or the inert gas and exhaust gas. In such a case, the above situation can be avoided by heating the hood 2. In addition, in order to achieve a desired temperature pattern, the hood 2 may be heated. A unit for heating is not particularly limited, and can be suitably selected depending on the purpose. However, the following means, for example, can be adopted, including the steps of: winding a line heater or pipe around the circumference of the hood 2; and subsequently causing steam to pass through the pipe. Both a pair of hoods 2 may be heated, or just one hood 2 may be heated. In addition, in the case of occurrence of a mass, an impact may be imparted to an appropriate location of the hood so as to dislodge the mass from the hood wall surface and the exhaust nozzle. A method for imparting an impact can employ a general method which has enough strength to be able to dislodge the mass by using an air knocker, a hammer, or a hammering device, etc.

The ring 3 has a groove 30 along a circumferential direction thereof which has an opening at the hood 2 side. The groove 30 has a substantially V- or U-shaped cross section. The groove 30 is created along the circumference of the ring 3. Both sides of the groove 30 come into contact with the internal surface of the hood 2. As used herein, the phrase "contact with" a hood refers to inclusion of embodiments in contact with the internal surface of the hood body as well as in contact with a flange or nozzle portion with which the hood is provided. A sealed chamber 300 is formed as a space surrounded by the hood 2 and the groove 30. An inert gas inlet 20 is installed at a position where inert gas can be supplied to the sealed chamber 300, and functions as a supply port for inert gas.

One or more of the inert gas inlets 20 may be allowed. When the shape and size of the ring 3 are taken into consideration, the number, size, and inert gas flow volume of the inert gas inlet 20 can be suitably adjusted. When an influence of a tiny amount of air contaminated from the outside of the groove 30, etc., is taken into consideration, it is preferable to circulate inert gas in the sealed chamber 300, and thus a gas outlet (not shown) is preferably installed. It is preferable to suitably adjust the position, number, and size of the gas outlet by taking into consideration the shape and size, etc., of the ring 3 in view of the following aspects: air contamination due to reflux of ambient air can be reduced; gas inside the sealed chamber 300 can be exhausted at a sufficient rate; a gas flow can be created in such a manner as to enable all the regions of the sealed chamber 300 to be uniformly replaced with inert gas; and others.

In addition, from the viewpoint of preventing damage to the ring 3 and dislocation from the hood 2 etc., it is preferable to dispose an inert gas inlet 20 at the deepest portion of the groove 30 or the center of the groove 30 in a width direction so as to blow the injected inert gas to these portions. According to this positioning, the inert gas allows the ring 3 to be uniformly pushed in its width direction. This can reduce deviation, which may occur when the inert gas blows only one side, of the ring 3 toward a width direction.

It is possible to install a nozzle to analyze gas components in the sealed chamber 300. This nozzle, for example, enables toxic gas to be detected in the case of there being a possibility of generating the toxic gas in the sealed chamber 300, and also can determine a concentration of oxygen contaminated in the sealed chamber 300 due to some reason. The inert gas inlet 20 and/or the outlet may play this function as well.

Inert gas is introduced into the sealed chamber 300. Accordingly, if there appears a gap between the ring 3 and the hood 2, the inert gas flows into the hood 2. Consequently, an inert gas atmosphere can be maintained in the specific space. In addition, the contact surface between the hood 2 and the ring 3 may wear due to continuous rotation over a long period. The calcination tube 1 and the hood 2 may expand/contract due to an increase or decrease in heat during calcination or at the termination of calcination. Also, the calcination tube 1 may be distorted for a moment or be deviated from the center of the rotation axis due to an impact imparted to the calcination tube 1 as described below. For the above cases, by appropriately keeping/adjusting gas pressures in the above specific space and sealed chamber 300, both sides of the groove 30 are suitably pushed onto the contact surface with the hood 2, which does not cause a gap and continues blocking contact with ambient air. That is, sealing characteristics are likely to remain the same.

A material of the ring 3 is not particularly limited. However, those having sufficient strength, heat resistance, and corrosion resistance and having flexibility and adhesive properties are preferable. Examples of the material include fluorine rubber, nitrile rubber, hydrogenated nitrile rubber, and ethylene propylene. The fluorine rubber is particularly preferable.

Figure 2:
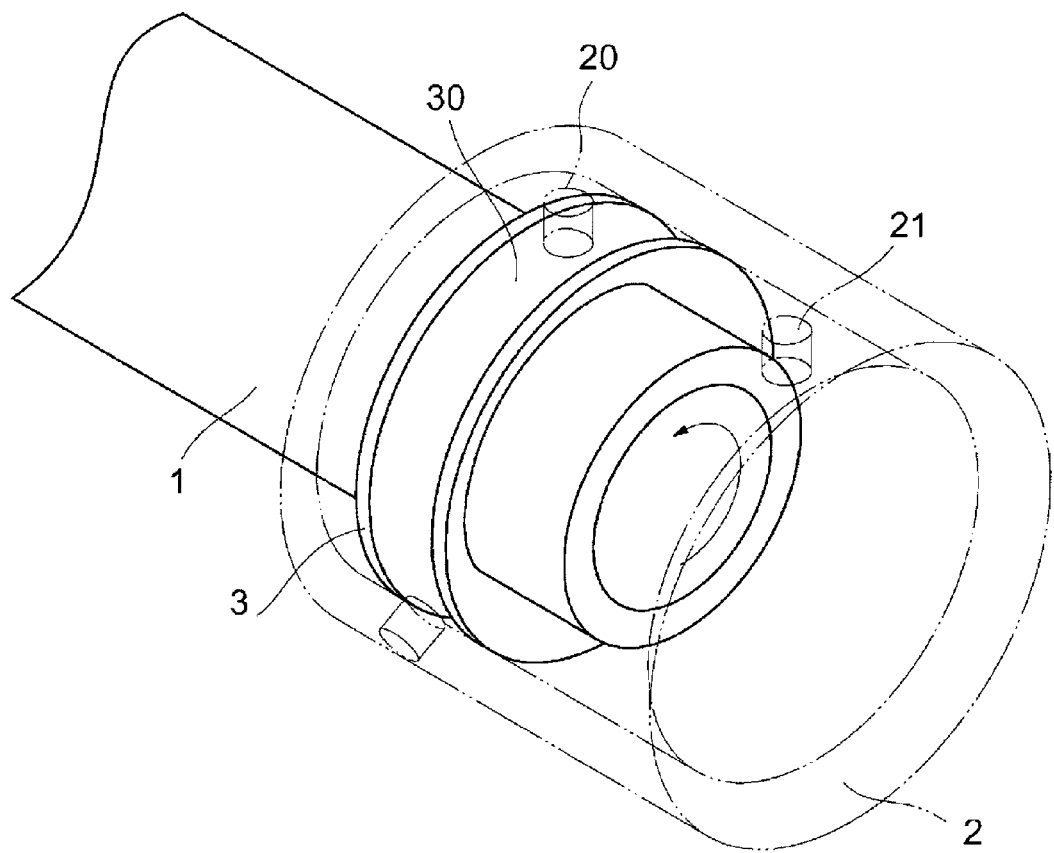
FIG. 2 is a schematic diagram perspectively showing one part of the calcination apparatus shown in FIG. 1.

FIG. 2 is a schematic perspective view perspectively showing a part of the calcination apparatus shown in FIG. 1. As shown in FIG. 2, the ring 3 is directly fixed to the calcination tube 1. Hence, both the ring 3 and the calcination tube 1 rotate along its circumferential direction. In contrast, the hood 2 does not rotate, so that friction is generated on the contact surface between the ring 3 and the hood 2. However, since the sealed chamber 300 is kept at a state in which inert gas is filled, occurrence of a gap between the ring 3 and the hood 2 only results in infiltration of the inert gas into the hood 2. Therefore, an atmosphere inside the calcination tube 1 is unaffected. In order to fix the ring 3 to the calcination tube 1, a ring 3 having an inner diameter approximately equal to an outer diameter of the calcination tube 1 may be fitted, or the ring 3 may be fitted by providing a groove which enables the ring 3 to fit into the calcination tube 1. Alternatively, a ring 3 having flexibility and an inner diameter smaller than an outer diameter of the calcination tube 1 may be fixed to the calcination tube 1 by using its flexibility.

Figure 3:
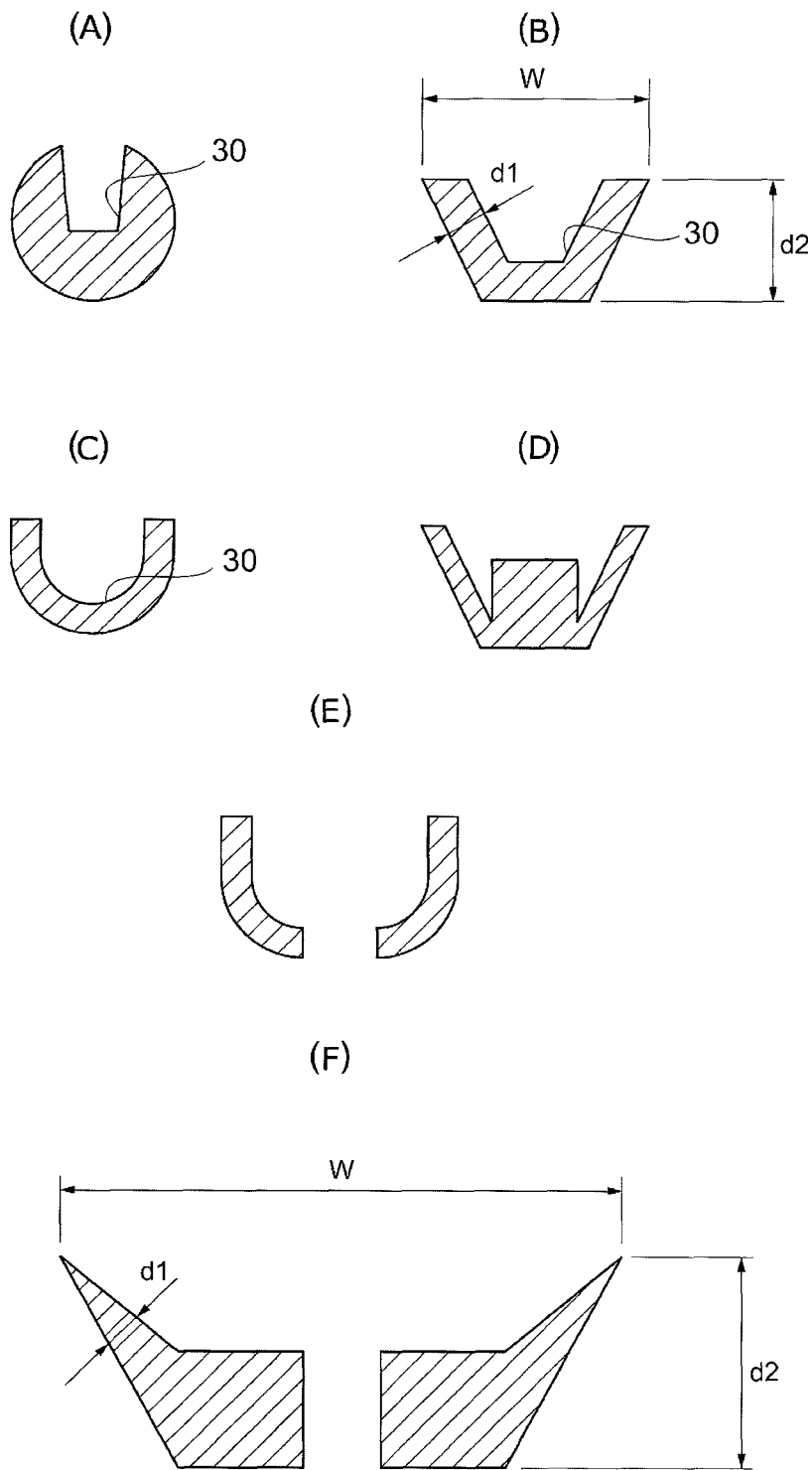
FIG. 3 is a schematic cross-sectional diagram showing examples of modified cross-sectional shapes of a ring according to the present embodiment.

Having a circumferential groove 30, the ring 3 may have any shape. FIG. 3 is schematic cross-sectional views showing cross-sectional shapes of the ring 3 of a modified embodiment. For example, as illustrated in FIGS. 3(A), (B), and (C), the cross-sectional shape of the ring 3 may be a circle with a notch, a V-shape having a straight line at the bottom, or U-shape. A shape illustrated in FIG. 3(D) may be allowed. The ring 3 may have various wall thicknesses depending on its shape. The wall thickness may be appropriately determined depending on, in addition to the shape of the ring 3, an inner diameter and length of the calcination tube 1 and/or the hood 2. Generally speaking, from the viewpoint of strength and sealing characteristics, the wall thickness of the thinnest portion (e.g., d1, in FIG. 3(B)) is preferably 0.1 mm or more. From the viewpoint of flexibility, the wall thickness of the thickest portion is preferably 200 mm or less, and the wall thickness is more preferably 0.5 to 50 mm. From the viewpoint of maintaining airtightness even at the time of an impact on the calcination tube 1, the wall thickness of the ring 3 is preferably 1.5 to 50 mm.

The width (e.g., w, in FIG. 3(B)) and the height (e.g., d2, in FIG. 3(B)) of the cross-section of the ring 3 are not particularly limited so long as they can keep sealing characteristics in a similar manner. Also, they can be appropriately determined depending on an inner diameter and length, etc., of the calcination tube 1 and/or the hood 2. In general, from the viewpoint of easily maintaining the strength, flexibility, and sealing characteristics, the width is preferably 10 to 500 mm, and the height is preferably 5 to 400 mm. From the viewpoint of maintaining airtightness even at the time of an impact on the calcination tube 1, the width and height of the ring 3 are preferably 20 to 200 mm and 10 to 150 mm, respectively.

Figure 4:
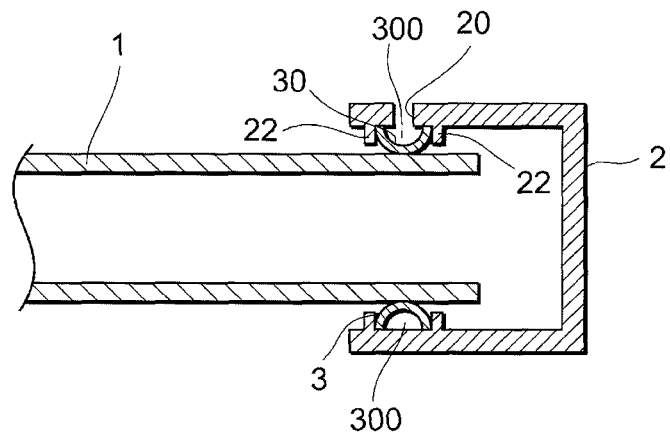
FIG. 4 is a schematic cross-sectional diagram partially showing another example of a calcination apparatus according to the present embodiment.

FIG. 4 is a schematic cross-sectional partial view showing another calcination apparatus of an embodiment of the present invention. The calcination apparatus shown in FIG. 4 has the same structure as in an embodiment of FIG. 1 except that the hood 2 is provided with a pair of flanges 22 which are engaged with the ring 3. Thus, only differences are described below. The flanges 22 are provided in such a manner as to protrude from the inner surface of the hood 2 toward an inside in a circumferential direction (i.e., toward an outer surface) of the calcination tube 1. It is preferable to have annular flanges 22 which are provided all over the inner surface of the hood 2 in a circumferential direction. The width between the first flange 22 and the second flange 22 is equal to the width of the ring 3, and both sides of the groove 30 come into contact with the first and second flanges 22. As shown in an apparatus of FIG. 4, the ring 3 comes into contact with the flanges 22, and the sealed chamber 300 is filled with inert gas to have a higher pressure in the sealed chamber 300 than environmental pressure. In these cases, the ring 3 whose width of the groove 30 is made to extend by a pressure is pushed against the flanges 22, so that an effect of blocking infiltration of ambient air by the ring 3 increases. At this time, from the viewpoint of preventing damage to the ring 3 and dislocation from the hood 2, etc., it is preferable to dispose an inert gas inlet 20 at the deepest portion of the groove 30 or the center of the groove 30 in a width direction so as to blow the injected inert gas to these portions. According to this positioning, the inert gas allows the ring 3 to be uniformly pushed against the flanges 22 in a width direction. This causes a situation in which the ring 3 is firmly fitted between both the flanges 22. As a result, dislocation, which may occur when the inert gas blows only one side, from the flange 22 can be reduced further.

Figure 5:
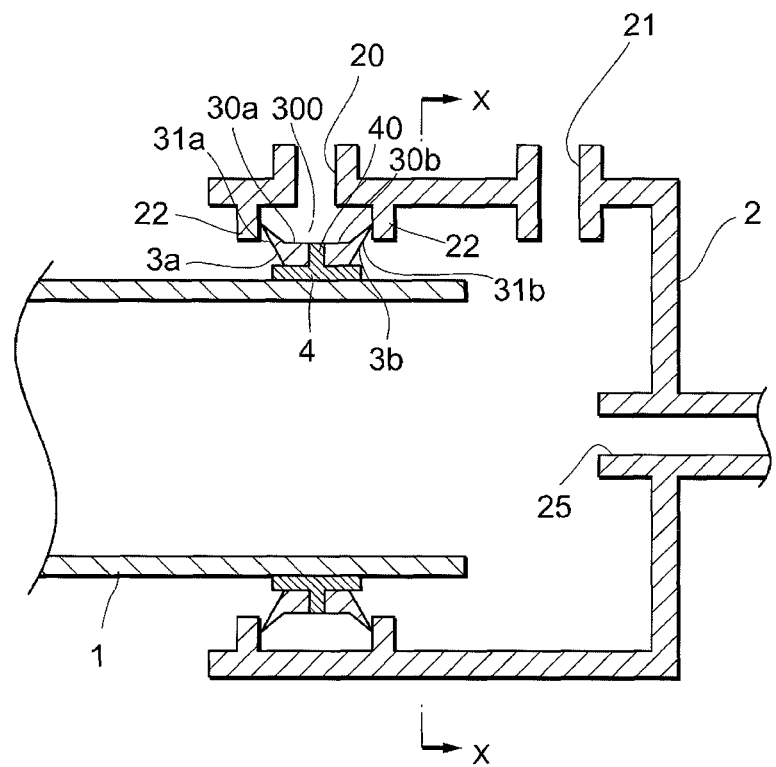
FIG. 5 is a schematic cross-sectional diagram partially showing still another example of a calcination apparatus according to the present embodiment.
Figure 7:
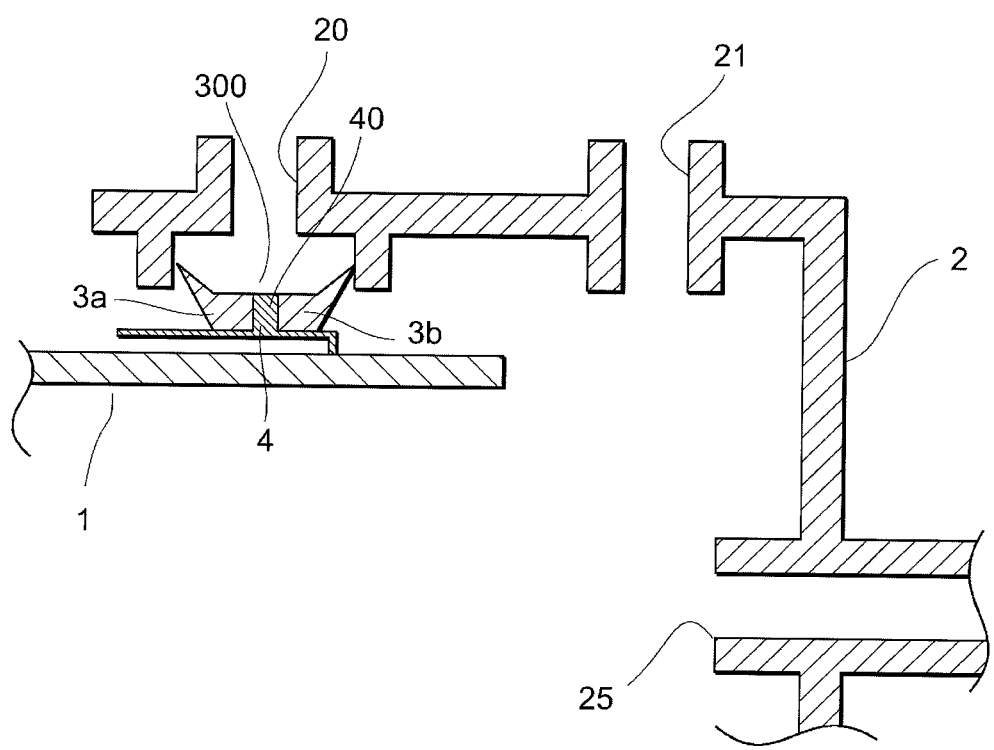
FIG. 7 is a schematic cross-sectional diagram partially showing one example of a case where a sealing support according to the present embodiment is hollow.

FIG. 5 is a schematic cross-sectional partial view showing a further additional calcination apparatus of an embodiment of the present invention. The calcination apparatus shown in FIG. 5 has the same structure as in an embodiment of FIG. 1 except that a pair of rings 3a and 3b is fixed to the calcination tube 1 via a sealing support 4. Thus, only differences are described below. The sealing support 4 is an annular member having an inner diameter equal to an outer diameter of the calcination tube 1, and is fixed to the circumference of the calcination tube 1 by welding, etc. A projection 40 is provided all over the circumference of the sealing support 4 in a circumferential direction. The projection 40 is interdisposed between the rings 3a and 3b. The projection 40 may be formed on the sealing support 4 as an integral part, or may be fixed to the sealing support 4 by using welding or screw cramp, etc. In an embodiment shown in FIG. 5, the sealing support 4 including the projection 40 is solid, but the sealing support 4 may be hollow. From the viewpoint of thermal conduction, preferred is a hollow one. FIG. 7 is a schematic cross-sectional partial view showing a hollow sealing support 4 as an embodiment. As shown in FIG. 7, the sealing support 4 may have an opening toward the center of the calcination tube 1 in a longitudinal direction.

The ring 3a and the ring 3b have a symmetrical cross-sectional shape, including bases 30a and 30b and arm members 31a and 31b which protrude from the bases 30a and 30b, respectively, in a oblique upward direction. Both the rings 3a and 3b are disposed to have a substantially V-shaped cross section. In an embodiment shown in FIG. 5, a surface is designed to be shared between the upper surface of bases 30a and 30b and the upper surface of the projection 40. If the position of the rings 3a and 3b can be fixed, the heights of the bases 30a and 30b and the height of the projection 40 of both the rings may be the same or different without a particular limitation.

As shown in FIGS. 3(E) and 3(F), the rings 3a and 3b may be designed to have a cross-sectional shape of a substantial "U" shape or "V" shape in a state in which two or more parts are combined. The rings 3a and 3b have various wall thicknesses d1 depending on their shape. For example, in the case of the shape illustrated in FIG. 3(F), the upper end portion of the arm member is thin, and the base is thick. However, either may be designed from the viewpoint of keeping sealing characteristics, and may be appropriately determined depending on the shape of the rings 3a and 3b, as well as, an inner diameter and length of the calcination tube 1 and/or the hood 2, etc. Generally speaking, from the viewpoint of strength and sealing characteristics, the wall thickness d1 of the thinnest portion is preferably 0.1 mm or more. From the viewpoint of flexibility, the wall thickness d1 of the thickest portion is preferably 200 mm or less and more preferably 0.5 to 50 mm. From the viewpoint of maintaining airtightness even at the time of an impact on the calcination tube 1, the wall thickness d1 of the rings 3a and 3b is preferably 1.5 to 50 mm.

The width w and the height d2 which combine those of rings 3a and 3b optionally via the projection 40 of the sealing support are not particularly limited in a similar manner so long as they can keep the sealing characteristics, and can be appropriately determined depending on an inner diameter and length of the calcination tube 1 and/or the hood 2, etc. In general, from the viewpoint of easily maintaining the strength, flexibility, and sealing characteristics, the width w is preferably 10 to 500 mm, and the height d2 is preferably 5 to 400 mm. From the viewpoint of maintaining airtightness even at the time of an impact on the calcination tube 1, the width w and the height d2 of the rings 3a and 3b are 20 to 200 mm and 10 to 150 mm, respectively.

In the calcination apparatus shown in FIG. 5, a pair of flanges 22 is provided in such a manner as to protrude from the inner surface of the hood 2 toward an inside in a circumferential direction (i.e., toward an outer surface) of the calcination tube 1. The flanges 22 are provided all over the inner surface of the hood 2 in a circumferential direction to be engaged with the rings 3a and 3b. The flanges 22 may be annular, and may preferably be toric. The outer diameter of the flange 22 is equal to an inner diameter of the hood 2. The width of the ring of the flange 22 is a little shorter than the distance from the hood 2 to the sealing support 4, and thus the flange 22 does not come into contact with the sealing support 4. The upper ends of the arm members 31a and 31b each contact both the flanges 22. A sealed chamber 300 which is surrounded by the hood 2, flanges 22, rings 3a and 3b, and the projection 40 of the sealing support 4 is formed.

Figure 6:
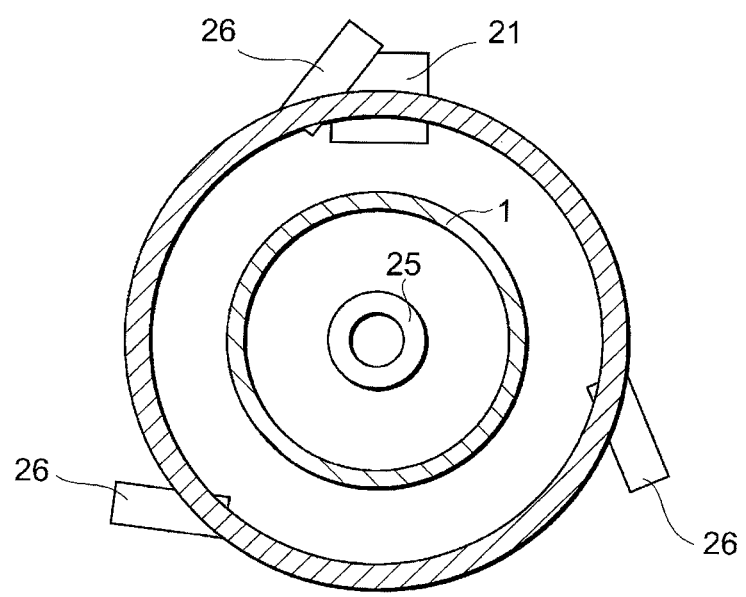
FIG. 6 is a schematic cross-sectional diagram showing a cross-section emerging by cutting along the line X-X in FIG. 5.

FIG. 6 shows an X-X cross section of an embodiment of FIG. 5. Although not shown in FIG. 5, the hood 2 has a plurality of inert gas inlets (air supply opening) 26 with equal intervals. Each inlet 26 has a nozzle which is disposed obliquely toward the outer surface of the hood 2. Each nozzle is connected at a substantially tangential angle toward the outer surface of the calcination tube 1. Consequently, when inert gas is fed from the nozzle of the respective inlets 26 into the inside of the hood 2, the gas circulates inside the hood. As a result, the above setting can prevent powder from being retained on the inner surface of the hood 2, etc., and can prevent powder from infiltrating from the contact surface between the ring 3 and the hood 2. An outlet (exhaust port) 25 is installed on an axis of the calcination tube 1. Inert gas is fed from the inlets 26 into the inside of the hood 2, then circulates inside the hood 2, and finally is exhausted outside the system from the outlet 25. It is to be noted that the number and position of the inlets 26 and the shape and installation angle of the nozzle are not limited to an embodiment as illustrated in FIG. 6. The number of the inlets 26 may be two or four or more. In addition, the nozzle may be attached perpendicularly to the outer surface of the hood 2. For example, the inert gas outlet 25 disposed at the hood 2 may be installed in the vicinity of the ring 3 and the circumference of the hood 2 instead of the center of the cross-sectional circle as illustrated in the X-X cross section. Also, the flow volume of the inert gas which flows through the respective inlets 26 may not be the same. In these cases, the inlets 26 preferably have unequal intervals. In addition, the inert gas outlet 25 may be disposed in the vicinity of the substantial center of the cross-sectional circle of the hood 2 at the X-X cross section and/or may be disposed away from the ring 3. In these cases, the nozzles are preferably disposed at equal intervals. Also, an equal volume of the inert gas is preferably made to flow from the respective nozzles.

Figure 8:
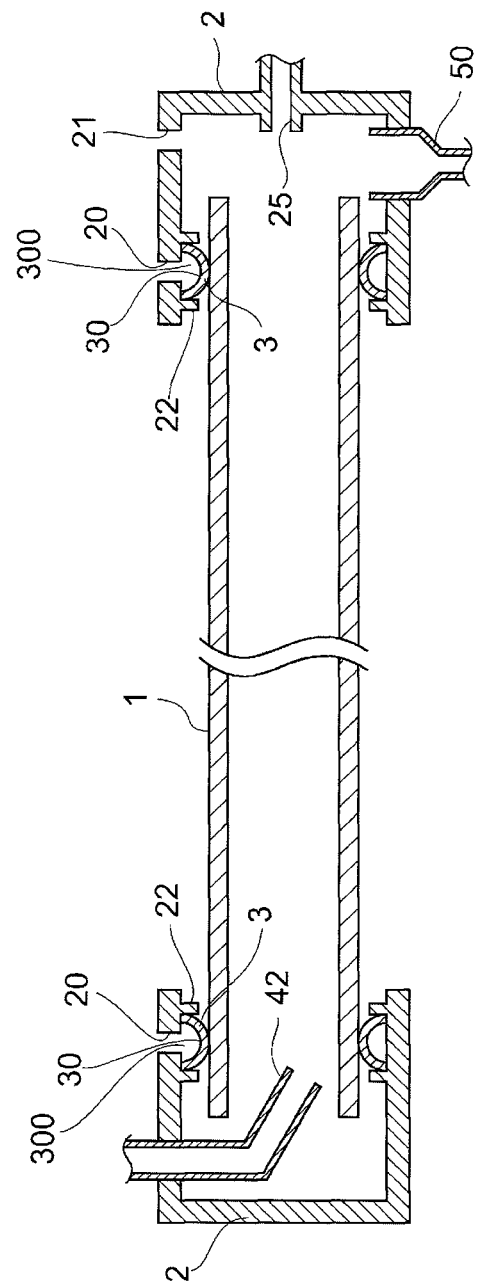
FIG. 8 is a schematic cross-sectional diagram partially showing further another example of a calcination apparatus according to the present embodiment.

FIG. 8 is a schematic cross-sectional view showing a still further additional calcination apparatus of an embodiment of the present invention. A calcination apparatus as shown in FIG. 8 has the same structure as in an embodiment illustrated in FIG. 1 except that a powder feeder 42 is installed at the left hood 2 (in FIG. 8, designated as a "hood 2a") and a collector 50 is installed at the right hood 2 (in FIG. 8, designated as a "hood 2b"). Thus, only differences are described below. The tubular feeder 42 penetrates through the upper surface of the hood 2a and has a lower end inserted into the calcination tube 1. The inserted end has an opening and powder can be fed into the calcination tube 1 at a constant rate. The collector 50 has a funnel-like structure having a wide upper end. The upper portion penetrates through the lower surface of the hood 2b and the collector 50 has an opening at an exit portion of the calcination tube 1. In the vicinity of the exit portion, a calcination subject of the calcination tube 1 passes through a mesh structure, and the collector 50 has an opening beneath the mesh. The size of the aperture of the mesh can be appropriately selected depending on the size of the calcination subject. The outlet 25 is disposed on an axis of the calcination tube 1, thereby preventing a calcination product from discharging from the outlet 25. In addition, the nozzle tip of the outlet 25 is positioned outside the edge face of the calcination tube 1, so that the gas flow inside the hood 2 is hard to be disturbed. Also, it is not necessary to dispose the nozzle tip outside the calcination tube 1. Components such as gas generated at a specific location in the calcination tube 1 during calcination may be intended to be selectively removed. The powder introduced into the calcination tube 1 or the powder to be discharged may be discharged from the nozzle. In these cases, the nozzle tip may stay inside the calcination tube 1 or may share the surface with the edge face of the calcination tube 1.

The feeder 42 and the collector 50 penetrate through the hoods 2a and 2b, respectively. This setting enables the inside of the calcination tube 1 to be kept under an inert gas atmosphere, and can continuously feed powder to the calcination tube 1 to yield a calcination product. The feeder 42 may include a gas-solid separator (not shown). In order to stably supply powder to the calcination tube 1 without having reflux of gas from the calcination tube 1 into the feeder 42, it is preferable to keep a pressure at the feeder 42 side under a pressure equal to or more than that of the specific space. In the case of inclusion of a gas-solid separator, it is preferable to keep a pressure inside the gas-solid separator at a pressure equal to or more than that of the above specific space.

The lengths of the hoods 2a and 2b in an axis direction (i.e., a longitudinal direction) of the calcination tube 1 may not be the same, and can be suitably adjusted depending on the shape and number, etc., of the feeder 42 and the collector 50, etc. The inside of the hood 2a and 2b can further include additional necessary equipment in an extent without affecting the contacting sites among the hoods 2a and 2b, the rings 3, and the calcination tube 1. For example, the additional equipment can suitably include a sensor casing to insert a thermocouple for measuring a temperature in the calcination tube 1, a mesh to remove a mass into the collector 50, and the like.

Figure 9:
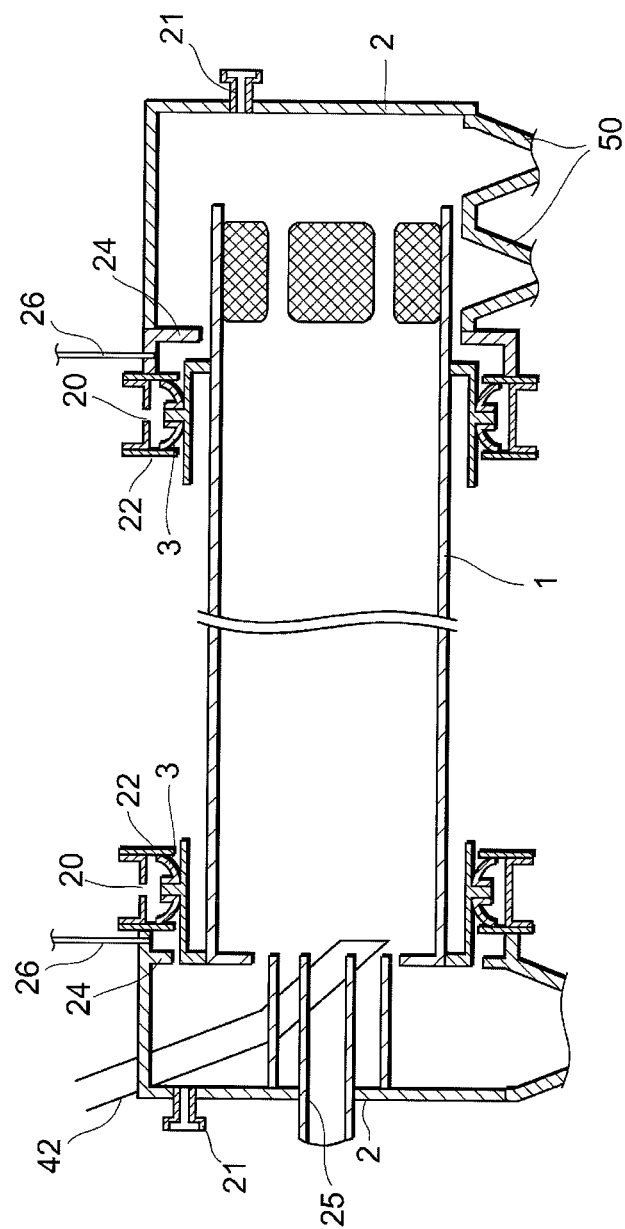
FIG. 9 is a schematic cross-sectional diagram showing still further another example of a calcination apparatus according to the present embodiment.

FIG. 9 is a schematic cross-sectional view showing a still further additional calcination apparatus of an embodiment of the present invention. A calcination apparatus as illustrated in FIG. 9 is substantially similar to an embodiment as illustrated in FIG. 8, except that the apparatus is different from an embodiment shown in FIG. 8 in the following points and includes: flanges 24 protruding from the inner surface of the hood 2 toward an inside in a circumferential direction (i.e., toward an outer surface) of the calcination tube 1 so as to protect the sealed chamber 300, the flanges 24 disposed at further outside the flanges 22; inert gas inlets 26; inert gas inlets 21, the position of which is modified and the inlets being included in both the hoods 2; and the outlet 25, the position of which is modified. Thus, only differences are described below.

The flanges 24 are provided in such a manner as to protrude from the inner surface of the hood 2 toward an inside in a circumferential direction (i.e., toward the outer surface) of the calcination tube 1. It is preferable to have annular flanges 24 which are provided all over the inner surface of the hood 2 in its circumferential direction. Having the flange 24 causes a partially separated space to be formed between the flange 22 and flange 24. This space is located so as to separate the sealed chamber 300 from the specific space. This space can prevent sealing characteristics from deteriorating. The deterioration is caused by infiltration of the powder from the calcination tube 1 into a gap between the ring 3 and the flange 22, thereby wearing the ring 3. It is preferable to prevent powder contamination by providing an inert gas inlet 26 shown in FIG. 6 at a partially separated space between the flange 22 and the flange 24. Since the flange 24 allows for separation from the specific space, this setting can reduce influences on a gas flow in the calcination tube 1 due to an inert gas flow which prevents the powder contamination.

The feeder 42 and the collector 50 may include transportation equipment (not shown) to transport powder to the calcination tube 1 and/or a powder storage container (not shown), etc. If the powder can be transported, the transportation equipment has no limitation, and can employ, for example, a pneumatic device which allows for transportation using a gas stream. In order to maintain a catalyst precursor and a calcination product under an inert gas atmosphere before and after calcination, it is a preferable embodiment to utilize the pneumatic device by using inert gas as a vehicle.

Between the pneumatic device and the feeder 42 and collector 50, it is preferable to have suitable equipment (e.g., a powder storage container which is connected to the specific space via a pipe, a powder feeder, and a gas-solid separator) to reduce infiltration of air or gas from the outside of the specific space and to reduce a pressure fluctuation effect. Examples of such equipment which can be suitably used include a rotary valve and a double damper. From the viewpoint of preventing gas circulation, the double damper is preferably used.

The feeder 42 and the collector 50 can include a supply device to supply powder at a constant rate. The supply device is not particularly limited, and can employ a common constant feeder. Examples of the supply device which can be suitably used include incidental equipment such as a cyclone and a pneumatic device and a loss-in-weight feeder from the viewpoint of powder being able to be supplied at a constant rate with high precision and without receiving a pressure effect.

Next, with regard to the above-described embodiments, an atmospheric pressure within the specific space and a pressure of the sealed chamber 300 are described. In order to maintain the specific space under an inert gas atmosphere, it is preferable to keep the specific space at a pressure higher than that of the outside of the space and to keep a state in which ambient air is unlikely to be contaminated. A method for keeping the specific space at a pressure higher than that of the outside of the space can employ, but is not limited to, a general method. For example, a flow control device and/or a pressure-regulating valve (orifice) are disposed at a gas injection side and/or a gas ejection side. It is also possible for a gas outlet to be connected to a pot which has been filled with water at an appropriate height, etc. A difference between an atmospheric pressure within the specific space and an atmospheric pressure outside the specific space refers specifically to a pressure difference P1 (hereinafter, simply referred to as a "pressure P1") represented by the following equation (1):

$$P1 = (\text{an atmospheric pressure within the specific space}) - (\text{an atmospheric pressure outside the specific space}) \qquad (1).$$

From the viewpoints of the specific space being able to be easily maintained under an inert gas atmosphere, the ring not being damaged, and the like, the pressure P1 is preferably more than 0 mm $H_2O$ and 900 mm $H_2O$ or less and more preferably more than 10 mm $H_2O$ and 700 mm $H_2O$ or less.

In a similar manner, in order to keep sealing characteristics of the contact surface between the ring 3 and the hood 2, it is preferable to keep a pressure of the sealed chamber 300 at a pressure higher than that of the outside of the sealed chamber. A method for keeping the sealed chamber 300 at a pressure higher than that of the outside can employ, but is not limited to, a general method. For example, a flow control device and/or a pressure-regulating valve (orifice) are disposed at a gas injection side and/or a gas ejection side. It is also possible for a gas outlet to be connected to a pot which has been filled with water at an appropriate height, etc. Furthermore, it is preferable to maintain a pressure of the sealed chamber 300 at a pressure higher than that of the above specific space. When one of the rings 3 (or either ring 3a or 3b) is worn or dislocated, a higher pressure of the sealed chamber 300 causes inert gas to flow into the specific space from the sealed chamber 300 and helps maintain an inert gas atmosphere. Therefore, the higher pressure is preferable. A difference between a pressure of the sealed chamber 300 and a pressure within the specific space refers specifically to a pressure difference P2 (hereinafter, simply referred to as a "pressure P2") represented by the following equation (2):

$$P2 = (\text{a pressure of the sealed chamber}) - (\text{a pressure within the specific space}) \qquad (2).$$

The pressure P2 is preferably more than 0 mm $H_2O$ and 500 mm $H_2O$ or less and more preferably more than 1 mm $H_2O$ and 200 mm $H_2O$ or less.

From the viewpoints of a calcination subject having stable and preferable performance being able to be produced, etc., it is preferable to keep an oxygen concentration within the specific space at 1000 ppm or less at the time of using a calcination apparatus. The oxygen concentration is more preferably 500 ppm or less and still more preferably 200 ppm or less.

Next, a unit for imparting an impact to the calcination tube 1, which means can be used in the above embodiments, are described. A calcination apparatus according to an embodiment of the present invention preferably includes a unit for directly or indirectly imparting an impact to the calcination tube 1. The unit for imparting an impact is not particularly limited so long as suitable impact force can be kept even for long-term continuous usage. Examples of the means which can be suitably used include an air knocker, a hammer, a hammering device, and the like. The hammer shape in the case of using, for example, a hammer or hammering device is preferably a shape which can efficiently deliver an impact, and is preferably a column whose cross-section is a square. A material for the impact tip portion which directly makes contact with the calcination tube 1 is not particularly limited if the material has sufficient heat resistance. Examples of the material which can be used include a common resin and a metal, which can endure an impact, and the like. Among them, the metal is preferable. Preferred is a metal having enough hardness not to be subjected to damage and deformation of the calcination tube 1. Those made of copper or SUS can be preferably used, and in particular the SUS is preferable. Any impact site may be allowed if the site is convenient for operation. The site may be directly located on the calcination tube 1 or may be located on a site via the hood 2. In order to maintain sealing characteristics of the contact surface between the ring 3 and the hood 2, the impact site is preferably located at a site other than a hood 2 portion which comes into contact with the ring 3. In order to be able to directly and efficiently deliver an impact to a calcination tube, the impact site is preferably located at a site which is not occupied by a heating furnace for the calcination tube.

The number of impact sites may be one or more. In order to efficiently transmit a vibration, an impact is imparted to the calcination tube 1 in a direction perpendicular to its rotational axis. The impact frequency is not particularly limited. However, adhesion in the calcination tube 1 tends to efficiently decrease, so that an impact is preferably constantly imparted to the calcination tube. Here, the phrase "an impact is constantly imparted" refers to imparting an impact at a frequency more than a certain number. An impact is imparted preferably once per between 1 second and 1 hour, more preferably once per between 1 second and 30 minutes, still more preferably once per between 1 second and 5 minutes, and still more preferably once per between 1 second and 1 minute. It is not necessary to impart an impact at an identical frequency, and the frequency may be at random. For example, after an impact is given once per 10 seconds, an impact is imparted twice or more per 10 seconds, and then the frequency returns at once per 10 seconds. The impact frequency is preferably appropriately adjusted depending on vibration acceleration, a powder depth of a catalyst precursor supplied to a calcination tube, a diameter, length, wall thickness, and material of a calcination tube, and a material, type, and shape of a device to impart an impact.

The impact renders "vibration acceleration" to the calcination tube 1. The "vibration acceleration" means an average of values obtained by measuring at a distance of L/4, 3L/8, L/2 from a powder inlet of the calcination tube in a direction parallel to a powder flow, the L representing the entire length of the calcination tube 1. Measurement points are set to the same positions as impact points in a cross-sectional direction of the calcination tube. The vibration acceleration can be determined using a vibrometer installed at the calcination tube. As a vibrometer, MD220, MD320, or MD550 manufactured by ASAHI KASEI TECHNOSYSTEM CO., LTD., can be used.

By using a calcination apparatus according to an embodiment of the present invention, an oxide catalyst precursor can be calcined to produce an oxide catalyst. When a redox number of an oxide catalyst is intended to be regulated during a calcination step, a preferable embodiment for oxide catalyst production is said to include a sealed chamber filled with inert gas and a step of calcining a catalyst precursor by using a calcination apparatus which can readily maintain an inert gas atmosphere. As used herein, the term "oxide catalyst" refers to a catalyst containing an oxide having one or more metal components. As described below, in the case of a catalyst in which a component functioning as a main catalyst is supported on a carrier, the term "oxide catalyst" means a concept including the main catalyst and the carrier. The term "catalyst precursor" refers to a compound generated during a step of producing an oxide catalyst.

Next, an embodiment of a process for producing a catalyst precursor is described. Then, an embodiment of a process for calcining the resulting catalyst precursor is illustrated.

(Step of Preparing a Raw Material Mixture)

First, a metal-component-containing raw material is dissolved in a solvent such as water, and then is mixed to yield a raw material mixture. In an embodiment of the present invention, the metal component may contain Mo, V, Nb, and Te and/or Sb.

The metal-component-containing raw material is not particularly limited, and for example, the following compounds can be used. Examples of a Mo raw material include molybdenum oxide, ammonium dimolybdate, ammonium heptamolybdate, phosphomolybdic acid, and silico molybdic acid. Among them, ammonium heptamolybdate can be preferable used. Examples of a V raw material include vanadium pentoxide, ammonium metavanadate, and vanadyl sulfate. Among them, ammonium metavanadate can be preferably used. Examples of an Nb raw material include at least one selected from the group consisting of niobic acid, inorganic acid salts of niobium and organic acid salts of niobium. Among them, niobic acid is preferable. The niobic acid is represented by $Nb_2O_5 \cdot nH_2O$, and is also referred to as niobium hydroxide or niobium oxide hydrate. Among them, it is preferable to use a niobium raw material containing dicarboxylic acid and a niobium compound and to use a niobium liquid raw material having dicarboxylic acid/niobium at a molar ratio of 1 to 4. As an Sb raw material, antimony oxide can be preferably used. Examples of a Te raw material include tellurium metal; inorganic tellurium compounds such as telluric acid, tellurium dioxide, and tellurium trioxide; and organic tellurium compounds such as methyl tellurol and dimethyl telluroxide. Among them, telluric acid can be preferably used. For every metal component, one or two or more kinds of the raw material can be used.

Hereinafter, a step of preparing a raw material mixture is specifically described by taking preparation of a raw material mixture containing Mo, V, Nb, and Sb as an example.

First, powders of ammonium heptamolybdate, ammonium metavanadate, and diantimony trioxide are added to water, and the mixture is heated to 80° C. or more to prepare a mixed solution (A). At this occasion, when a catalyst contains, for example, Te, B, and Ce, telluric acid, boric acid, and cerium nitrate can be simultaneously added thereto.

Next, niobic acid and oxalic acid are heated and stirred in water to prepare a mixed solution (B). The mixed solution (B) can be produced by a procedure described below. Specifically, niobic acid and oxalic acid are added to water, and the mixture is stirred to yield an aqueous solution or an aqueous suspension. In the case of suspension, a small amount of ammonia water may be added or heating may be carried out to promote solubilization of a niobium compound. Then, this aqueous solution or aqueous suspension is cooled and filtered to yield a niobium-containing solution. The cooling is simply carried out on ice. The filtering is simply carried out by decantation or filtration. An oxalic acid can be appropriately added to the resulting niobium-containing solution to prepare a mixture at a suitable oxalic acid/niobium ratio. The molar ratio of oxalic acid/niobium is preferably 2 to 5 and more preferably 2 to 4. Furthermore, hydrogen peroxide may be added to the resulting niobium-mixed solution to prepare a mixed solution (B). At this occasion, the molar ratio of hydrogen peroxide/niobium is preferably 0.5 to 20 and more preferably 1 to 10.

After that, in order to achieve a composition of interest, the mixed solution (A) and the mixed solution (B) are blended to yield a raw material mixture. When a catalyst contains, for example, W and/or Mn, a W-containing compound is suitably mixed to yield a raw material mixture. Examples of the W-containing compound which can be suitably used include ammonium metatungstate. Examples of a Mn-containing compound which can be suitably used include manganese nitrate. A compound containing W and/or Mn can be added to the mixed solution (A), or can be added at the time of blending the mixed solution (A) with the mixed solution (B). When an oxide catalyst is supported on a silica carrier, a raw material mixture can be prepared in such a manner as to include a silica sol. In that case, the silica sol can be appropriately added.

In addition, in the case of using antimony, hydrogen peroxide is preferably added to the mixed solution (A) or a solution containing components of the mixed solution (A) during formulation processes. At this occasion, the ratio of $H_2O_2/Sb$ (a molar ratio) is preferably 0.01 to 5 and more preferably 0.05 to 4. At this time, the stirring is preferably carried out at 30° C. to 70° C. for 30 minutes to 2 hours. The catalyst raw material mixture obtained in such a manner may be a uniform solution, but is usually slurry.

(Drying Step)

The raw material mixture obtained in the above step is dried to yield a dried catalyst precursor. The drying can be performed by a publicly known procedure. Examples of the procedure include spray drying and evaporation to dryness. However, it is preferable to carry out spray drying to produce a microspherical dried catalyst precursor. Nebulization used in the spry drying can be carried out by a centrifugation process, a two-fluid nozzle process, or a high-pressure nozzle process. As a heat source for drying, air which has been heated with steam or an electric heater, etc. can be used. The dryer inlet temperature of a spray dryer is preferably 150 to 300° C. The dryer outlet temperature is preferably 100 to 160° C.

(Calcination Step)

Next, by using a calcination apparatus according to the above-described embodiments of the present invention, a catalyst precursor is calcined to yield a calcination product. Specifically, the process includes the steps of: feeding a catalyst precursor to a calcination tube 1 from its first end; causing the catalyst precursor to pass through a specific space before and after calcination in the calcination tube 1 to yield a calcination product; and discharging the resulting calcination product from a second end of the calcination tube 1. This process enables an oxide catalyst of a calcination product to be produced.

The calcination of the catalyst precursor can be carried out by either continuous calcination or batch calcination. Usually, the continuous calcination can produce a larger amount of the catalyst than the batch calcination. Unfortunately, the continuous calcination more readily causes a variation of its retention time and calcination temperature, etc. So, it tends to be difficult to calcinate all the catalyst precursors at an optimal calcination time and calcination temperature. Because of this, in the case of having an identical catalyst composition and calcination temperature for continuous calcination, it may be difficult to produce a yield equivalent to that of batch calcination.

In the case of continuous calcination, a weir plate having, in the central portion, a hole through which a catalyst precursor and/or an oxide catalyst can flow may be disposed in the calcination tube 1 in a direction perpendicular to a catalyst precursor flow. Thus, the calcination tube 1 can be separated into two or more areas. Providing the weir plate is likely to reserve a retention time in the calcination tube 1. The number of weir plates may be one or more. A material for the weir plate is preferably a metal. The identical material as for the calcination tube 1 can be suitably used. As the materials for the calcination tube 1, the weir plate, and the hood, SUS310S and/or SUS304 are preferable from the viewpoints of heat resistance, impact resistance, and corrosion resistance. The height of the weir plate can be adjusted depending on a retention time to be reserved. For example, a rotary furnace includes an SUS calcination tube 1 having an inner diameter of 150 mm and a length of 1150 mm. A catalyst precursor is fed into the rotary furnace at 250 g/hr. In this case, the height of the weir plate is preferably 5 to 50 mm, more preferably 10 to 40 mm, and still more preferably 13 to 35 mm. The thickness of the weir plate is not particularly limited, and is preferably adjusted depending on the size of the calcination tube 1. For example, in the case of a rotary furnace including an SUS-made calcination tube 1 having an inner diameter of 150 mm and a length of 1150 mm, the thickness of the weir plate is preferably between 0.3 mm and 30 mm and more preferably between 0.5 mm and 15 mm.

During the step of calcination, in order to prevent a crack and break, etc., of a catalyst precursor and to achieve uniform calcination, the calcination tube 1 is preferably made to rotate along a longitudinal axis thereof. The rotation speed of the calcination tube is preferably 0.1 to 30 rpm, more preferably 0.3 to 20 rpm, and still more preferably 0.5 to 10 rpm.

As to calcination of a dried catalyst precursor, it is preferable to continuously or intermittently raise a temperature from 400° C. or lower to a temperature range between 550 and 800° C.

In the case of batch calcination, the feed rate of inert gas per kg catalyst precursor is preferably 50 NL/hr or more, more preferably 50 to 5000 NL/hr, still more preferably 50 to 4000 NL/hr (the "NL" means a "L" which is determined at standard temperature and pressure conditions (i.e., a "L" which is determined at 0° C. and 1 atm)). In the case of continuous calcination, the feed rate of inert gas per kg catalyst precursor is preferably 50 NL or more, more preferably 50 to 5000 NL, still more preferably 50 to 4000 NL (the "NL" means a "L" which is determined at standard temperature and pressure conditions (i.e., a "L" which is determined at 0° C. and 1 atm)). At this time, the inert gas and the catalyst precursor may flow either in a counter current direction or in a parallel current direction. However, when gas components generated from the catalyst precursor and a small amount of air containing the catalyst precursor are taken into consideration, a counter current contact is preferable. The type of the inert gas is not particularly limited. Examples of the inert gas include helium, nitrogen, argon, carbon dioxide, and the like. However, nitrogen is preferable.

The calcination step can be carried out by even one step. However, in order to readily and efficiently adjust a rate of reduction of a catalyst to an appropriate degree, pre-stage calcination can be preferably carried out before main calcination. The pre-stage calcination and the main calcination may be carried out continuously. Also, the main calcination may be performed again after the pre-stage calcination has been once terminated. In addition, each of the pre-stage calcination and the main calcination may have several steps. Between the pre-stage calcination and the main calcination, the main calcination has a larger effect of imparting an impact to the calcination tube 1.

When calcination is carried out in separate occasions of the pre-stage calcination and the main calcination, a calcination apparatus common to the pre-stage calcination and the main calcination may be used. The pre-stage calcination is carried out for a certain period of time. Powder after the pre-stage calcination (hereinafter, referred to as pre-stage calcination powder) is collected. After the pre-stage calcination has been completed, the calcination apparatus is reset to a temperature condition for the main calcination. Then, the main calcination may be carried out by feeding the pre-stage calcination powder. Alternatively, the pre-stage calcination and the main calcination may employ different calcination apparatuses. From the viewpoint of improving a catalyst production efficiency and production amount and the viewpoint of avoiding contamination of a catalyst precursor/catalyst which has remained during the pre-stage calcination/main calcination, it is preferable to use separate calcination apparatuses.

The hood 2, at the powder injection side of a calcination apparatus, that is used in the pre-stage calcination and the main calcination is preferably heated so as not to inhibit a gas or powder flow or so as not to clog a powder supply port or an inert gas inlet or outlet due to generation of a mass, together with the powder, caused by condensation of water and ammonia gas produced in the calcination tube 1. From the viewpoint of preventing the condensation, the wall surface of the hood 2 is preferably heated to about 80 to 300° C. Examples of the unit for heating include a line heater and a steam piping which are installed on a hood circumference.

The pre-stage calcination is preferably performed under an inert gas circulation. The heating temperature is in a range of preferably 250° C. to 400° C. and more preferably 300° C. to 400° C. A constant temperature in a range of 250° C. to 400° C. should be preferably maintained. However, the temperature may fluctuate within a range of 250° C. to 400° C. A moderate temperature rise or temperature fall may be allowed. The retention time of the heating temperature is preferably 30 minutes or more and more preferably 3 to 12 hours.

The temperature pattern until a pre-stage calcination temperature has been reached may be a linear temperature rise pattern or a temperature rise pattern having a concave or convex curve. In addition, during the temperature rise, there may be a time of a temperature fall. Alternatively, the temperature rise and temperature fall may be repeated. Furthermore, components included in dried powder and/or a catalyst precursor during a temperature rise process may cause an endothermic reaction, which results in a temporal temperature fall. Moreover, to a calcination atmosphere under an inert gas circulation may be added an oxidizing component (e.g., oxygen) or a reducing component (e.g., ammonia), if desired.

From the viewpoint of an easy-to-regulate temperature which causes an exothermic or endothermic reaction during calcination, the heating process is preferably an external heating process. Also, an electric furnace can be suitably used.

The average programming rate during a temperature rise until a pre-stage calcination temperature has been reached is preferably, but is not limited to, 0.1 to 15° C./min, more preferably 0.5 to 5° C./min, and still more preferably 1 to 2° C./min.

The main calcination can be carried out preferably under an inert gas circulation, and the heating temperature is preferably 550 to 800° C., more preferably 580 to 750° C., still more preferably 600 to 720° C., and still more preferably 620 to 700° C. It is preferable to hold the heating temperature at a constant temperature within a temperature range of 620 to 700° C. However, the temperature may fluctuate within a range of 620° C. to 700° C. A moderate temperature rise or temperature fall may be allowed. The main calcination time is 0.5 to 20 hours and preferably 1 to 15 hours. Moreover, to a calcination atmosphere under an inert gas circulation may be added an oxidizing component (e.g., oxygen) or a reducing component (e.g., ammonia), if desired. The temperature pattern until a main calcination temperature has been reached may be a linear temperature rise pattern or a temperature rise pattern having a concave or convex curve. From the viewpoint of an easy-to-regulate temperature, the heating process is preferably an external heating process. Also, an electric furnace can be suitably used.

The average programming rate during a temperature rise until a main calcination temperature has been reached is preferably, but is not limited to, 0.1 to 15° C./min, more preferably 0.5 to 10° C./min, and still more preferably 1 to 5° C./min.

The average temperature fall rate after the main calcination is preferably 0.01 to 1000° C./min, more preferably 0.05 to 100° C./min, still more preferably 0.1 to 50° C./min, and still more preferably 0.5 to 10° C./min. In addition, it is preferable to keep a temperature lower than a temperature of the main calcination once. The retention temperature is lower than a temperature of the main calcination by preferably 5° C., more preferably 10° C., and still more preferably 50° C. The retention time is preferably 0.5 hour or more, more preferably 1 hour or more, still more preferably 3 hours or more, and still more preferably 10 hours or more.

When the calcination tube 1 is separated by weir plates, a catalyst precursor continuously passes through at least two areas, preferably 2 to 20 areas, and more preferably 4 to 15 areas. The temperature of each area can be regulated. For example, seven weir plates are disposed in the calcination tube 1 of a heating furnace so as to have its portion divided by eight equal areas. In the case of using the calcination tube 1 having the eight areas, in order to obtain the desired calcination pattern, the above parameters can be adjusted as follows. As for the pre-stage calcination, the temperatures detected by a thermocouple, which has been inserted into the center of each area including a catalyst precursor retained in the calcination tube 1, are preferably adjusted to; (from the catalyst-precursor-feeding side) area 1: 100 to 300° C., area 2: 150 to 400° C., area 3: 200 to 400° C., area 4: 200 to 400° C., area 5: 200 to 400° C., area 6: 200 to 400° C., area 7: 200 to 400° C., and area 8: 200 to 400° C. As for the main calcination, the temperature is preferably adjusted in a similar manner to area 1: 350 to 700° C., area 2: 400 to 750° C., area 3: 550 to 750° C., area 4: 550 to 750° C., area 5: 400 to 700° C., area 6: 400 to 700° C., area 7: 400 to 700° C., and area 8: 350 to 700° C. In addition, during the main calcination, the temperature at the wall surface of the calcination tube 1 having a contact with the catalyst precursor is preferably adjusted so as not to destroy a catalyst-precursor-derived crystal formed during calcination by excessive heat. The temperature at a position having the highest temperature on the wall surface of the calcination tube 1 is preferably 600 to 800° C. and more preferably 630 to 750° C.

When the oxide catalyst and/or the catalyst precursor contains a metal component producing a compound having a lower melting point than the calcination temperature, the compound having a lower melting point than the calcination temperature is likely to be generated during the calcination step. During the calcination, this compound is going to melt. This causes the oxide catalyst and the catalyst precursor, etc., to adhere and fuse to the inner wall of the calcination tube to form a mass. In particular, in the case of the continuous calcination, this is responsible for poor heat transfer, a decreased retention time, and an unstable powder flow. This makes it difficult to stably perform calcination at a desired temperature. In this case, it provides a preferable embodiment to perform calcination while imparting an impact to the calcination tube 1.

More specifically, a catalyst-constituent-element-containing metal oxide whose melting point is lower than the calcination temperature cause a problem of adhesion of the oxide catalyst and/or the catalyst precursor. The term "melting point of a catalyst-constituent-element-containing metal oxide" means a melting point when a metal element included in the oxide catalyst and/or the catalyst precursor forms a simple oxide (i.e., an oxide having only two components: a single metal component and oxygen). When one or more metal components form simple oxides having multiple composition formulae, the above-defined melting point refers to a melting point of an oxide having the lowest melting point among them. For example, according to Phase Diagrams for Ceramists (American Ceramic Society), molybdenum oxides have melting points: $MoO_2$ (818° C.) and $MoO_3$ (782±5° C.), and antimony oxides have melting points: $Sb_2O_3$ (655° C.) and $Sb_2O_5$ (525° C.). The melting point of the catalyst-constituent-element-containing metal oxide is (782-5° C. in the case of inclusion of molybdenum, is 525° C. in the case of inclusion of antimony, and is 525° C. in the case of inclusion of both the elements. Specifically, when the oxide catalyst contains Mo, Sb, V, and Nb and the calcination temperature is 650° C., the melting point of a simple oxide of antimony (diantimony pentaoxide), which is lower than the calcination temperature, meets a condition of "carrying out calcination at a temperature equal to or higher than the melting point of a catalyst-constituent-element-containing metal oxide". In addition, according to the above publication, the melting point of niobium oxide $Nb_2O_5$ is 1510° C., and the melting point of vanadium oxide $V_2O_5$ is 685° C. Also, the "calcination temperature" refers to a highest temperature of the oxide catalyst and/or the catalyst precursor in the calcination tube. In the case of batch calcination, the calcination temperature can be measured with a thermocouple inserted into the oxide catalyst and/or the catalyst precursor. In the case of continuous calcination, the oxide catalyst and/or the catalyst precursor flow through the calcination tube while having their deposition. The calcination temperature can be measured with a thermocouple inserted into the deposited oxide catalyst and/or catalyst precursor.

The total mass ratio of all the metal elements in which the calcination temperature is equal to or higher than the melting temperature of their metal oxides to the overall metal elements included in the oxide catalyst seems to affect how likely the oxide catalyst and/or the catalyst precursor are to adhere or fuse during calcination. That is, the oxide catalyst and/or catalyst precursor that has a low ratio of inclusion of compounds containing constituent elements having a low melting point are generally hard to adhere or fuse to the inner wall of the calcination tube. In contrast, a high ratio causes the oxide catalyst and/or catalyst precursor to readily adhere or fuse.

In order to effectively prevent the oxide catalyst and/or catalyst precursor from adhering by imparting an impact to the calcination tube 1, the "f" is preferably determined by the following equation:

$$f=(\text{vibration acceleration})/C \qquad (3),$$

wherein the vibration acceleration refers to vibration acceleration ($m/s^2$) of the impact imparted to the calcination tube; and the C denotes a total mass (% by mass) of all the metal elements in which the calcination temperature is equal to or higher than the melting temperature of their metal oxides based on the overall mass of the oxide catalyst.

In the case of a catalyst, which contains Mo, V, and Sb, used for producing acrylonitrile, although f is dependent on their composition ratio, it is preferable to satisfy an equation: $0.08 \le f \le 50$. The f satisfies more preferably $0.1 \le f \le 40$ and still more preferably $0.2 \le f \le 30$. If there is an element in which the calcination temperature is equal to or higher than the melting temperature of its metal oxide among the metal elements included in the oxide catalyst (catalyst constituent elements), the element melts. This causes the oxide catalyst and catalyst precursor, etc., to adhere and fuse to the inner wall of the calcination tube 1 to readily form a mass. When the f is 0.08 or more, the impact is more sufficient, so that the catalyst and/or the catalyst precursor are not readily attached to the wall surface of the calcination tube 1. In addition, the attached powder can be away from excessive calcination, and the unattached powder that passes through the inside can be prevented from flowing without sufficient heat transfer through the inside of the calcination tube. As a result, either powder further allows for calcination at a desired calcination temperature, so that desired performance can be easily achieved. On the other hand, when the f is 50 or less, the calcination tube 1 is not easily damaged or deformed. In addition, an impact-induced crack of particles flowing in the calcination tube 1 can be inhibited. The particle shape can remain in a good condition during a fluidized bed reaction. Also, flow disturbance due to scattering in a counter direction to the flow can be prevented from occurring. Damage and/or distortion of the calcination tube 1, the ring 3, and the hood 2 can be reduced. Moreover, the sealing characteristics at the contact surface between the ring 3 and the hood 2 can be further effectively preserved. Because of the above, calcination can be carried out at a desired calcination time and under a desired calcination atmosphere, so that a decrease in the catalytic performance can be further prevented.

By imparting an impact according to the vibration acceleration of the above formula (3) to the calcination tube 1 during the calcination step, their adhesion to the inner wall of the calcination tube 1 and generation of a mass as described above can be reduced. From this viewpoint, not only in the case of "carrying out calcination at a temperature equal to or higher than the melting point of the catalyst-constituent-element-containing metal oxide", but also in the case where a compound generated during the calcination step has the same or lower melting point than the calcination temperature, delivering an impact to the calcination tube can exert an effect of preventing their adhesion.

The impact imparted to the calcination tube 1 depends on: the depth of deposition (powder depth) of the catalyst precursor which has been fed into the calcination tube 1; the diameter, length, wall thickness, and material of the calcination tube 1; the material, type, shape, position of a device which imparts an impact; the impact frequency; and the like. Thus, it is preferable to suitably determine the impact by considering these properties.

In the case of an oxide catalyst containing Mo and Sb, Mo and Sb included in the catalyst and/or catalyst precursor may melt. This causes the oxide catalyst and/or catalyst precursor, etc., to adhere and fuse to the inner wall of the calcination tube 1 to readily form a mass. Thus, the "C" in the formula (3) can be set forth as C=A+B. Here, the "A" and "B" denote A % by mass of Mo included in the oxide catalyst and B % by mass of Sb included in the oxide catalyst, respectively.

As used herein, the term "A % by mass of Mo included in the oxide catalyst" means a mass ratio of an Mo metal atom to the oxide catalyst when each constituent element of the oxide catalyst is presumed to have a maximum oxidation number (i.e., the sum of mass ratios of an oxide of each component, the oxide having a maximum oxidation number). Specifically, the term means A=((a ratio of mass of Mo to mass of an oxide catalyst)×100% by mass). It is to be noted that when the oxide catalyst is supported on a carrier, a ratio of the carrier (% by mass) is subtracted from the total (100% by mass). That is, the term refers to A=((a ratio of mass of Mo atom to mass of an oxide catalyst)×(100−a ratio of a carrier) % by mass). For example, in the case of an oxide catalyst represented by $Mo_1V_{0.23}Nb_{0.086}Sb_{0.27}O_n/43\%$ by mass of $SiO_2$, each constituent component is presumed to have $MoO_3$, $VO_{2.5}$, $NbO_{2.5}$, and $SbO_{2.5}$, and "A" is calculated by using the following equation:

A=(Mo atomic weight×1)/(MoO₃ molecular weight×
1+VO₂.₅ molecular weight×0.23+NbO₂.₅
molecular weight×0.086+SbO₂.₅ molecular
weight×0.27)×(100−43)% by mass.

In the oxide catalyst, it is impossible to verify how many oxygen bonds to each component. Accordingly, it is presumed to have $MoO_3$, $VO_{2.5}$, $NbO_{2.5}$, and $SbO_{2.5}$, and a mass ratio of Mo to the oxide catalyst is defined by calculation.

In addition, the term "B % by mass of Sb included in the oxide catalyst" means a mass ratio of an Sb metal atom to the oxide catalyst when each constituent element of the oxide catalyst is presumed to have a maximum oxidation number. Hence, in the case of the above example, "B" is determined by using the following equation.

B=(Sb atomic weight×0.27)/(MoO₃ molecular
weight×1+VO₂.₅ molecular weight×0.23+NbO₂.₅
molecular weight×0.086+SbO₂.₅ molecular
weight×0.27)×(100−43)% by mass.

[Oxide Catalyst]

Examples of an oxide catalyst can include a compound containing molybdenum, vanadium, niobium, and antimony, the compound represented by a formula:

$$Mo_1V_aNb_bSb_cY_dO_n \quad (4),$$

wherein Y represents at least one element selected from the group consisting of Mn, W, B, Ti, Al, Te, alkali metals, alkali earth metals, and rare earth metals; a, b, c, d, and n each represent an atom ratio of V, Nb, Sb, or Y per molybdenum (Mo) atom, and preferably satisfy $0.1 \leq a \leq 1$, $0.01 \leq b \leq 1$, $0.01 \leq c \leq 1$, and $0 \leq d \leq 1$; n represents the number of oxygen atoms determined using a valence of a constituent element other than oxygen.

The atom ratios (a, b, c, and d) per Mo atom are preferably $0.1 \leq a \leq 1$, $0.01 \leq b \leq 1$, $0.01 \leq c \leq 1$, and $0 \leq d \leq 1$, respectively, more preferably $0.1 \leq a \leq 0.5$, $0.01 \leq b \leq 0.5$, $0.1 \leq c \leq 0.5$, and $0.0001 \leq d \leq 0.5$, and still more preferably $0.2 \leq a \leq 0.3$, $0.05 \leq b \leq 0.2$, $0.2 \leq c \leq 0.3$, and $0.0002 \leq d \leq 0.4$.

A dried catalyst precursor is calcined using the above-described calcination apparatus to yield an oxide catalyst. Then, the resulting catalyst can be used in an oxidation or ammoxidation reaction of an alkane and/or an alkene to produce corresponding unsaturated acid or unsaturated nitrile.

In the case of an oxide catalyst used for producing acrylonitrile by an ammoxidation reaction of propane, the rate of reduction of the catalyst affects its catalytic performance, so that a redox regulation at the time of catalyst preparation is critical. Use of a calcination apparatus according to an embodiment of the present invention enables a calcination atmosphere to be kept under an inert gas atmosphere. This is preferable because it is easy to regulate a redox during the calcination step.

Calcination is preferably carried out at a rate of reduction of the resulting oxide catalyst precursor and/or oxide catalyst of 8 to 12%, at a specific surface area of the oxide catalyst of 5 to 30 m²/g. Having a rate of reduction of 8 to 12% can achieve a sufficient activity and a sufficient yield of a product of interest, which can prevent the catalyst from deteriorating at the reaction initiation and during the reaction. Having a specific surface area of 5 to 30 m²/g can exert effects of further achieving a sufficient activity, further reducing the deterioration, and further increasing the yield. With regard to an effect of adding a molybdenum compound so as to keep the yield during an oxidation or ammoxidation reaction, its effect can be sufficiently exerted and any rapid deterioration is not exhibited. So, the additive amount of the molybdenum compound and the frequency of addition can be decreased. This reason remains elusive. However, having a specific surface area at smaller than 5 m²/g may achieve a smaller active surface of an active species which controls the reaction. Thus, the effect of adding the molybdenum compound is presumed to be unlikely to be exerted. In addition, in one hand, when the specific surface area is larger than 30 m²/g, the active surface of the active species increases. On the other hand, the molybdenum is presumed to rapidly escape from the active surface. The rate of reduction of the oxide catalyst and catalyst precursor is calculated by the following equation (6):

$$\text{Rate of reduction (\%)} = ((n_0 - n)/n_0) \times 100 \quad (6),$$

wherein n represents the number of oxygen atoms achieving a valence of constituent elements other than oxygen in the oxide catalyst or catalyst precursor; $n_0$ represents the number of oxygen atoms required when constituent elements other than oxygen in the oxide catalyst or catalyst precursor have the respective maximum oxidation numbers.

When the rate of reduction is calculated, a value of $(n_0-n)$ as in the above formula (6) is obtained by carrying out redox titration of a sample with $KMnO_4$. In addition, regarding any of the catalyst precursor before completion of calcination and the oxide catalyst after completion of calcination, the value of $(n_0-n)$ can be determined by the redox titration. However, as to redox titration measurements, the catalyst precursor before completion of calcination and the catalyst after completion of calcination have different measurement conditions. Regarding each of the catalyst precursor before completion of calcination and the catalyst after completion of calcination, an example of the measurement procedure is described below.

For example, a rate of reduction of the catalyst precursor before completion of calcination is determined as follows.

First, about 200 mg of a sample is weighed precisely and added to a beaker. An excessive amount of a $KMnO_4$ aqueous solution having a known concentration is added thereto. Next, to the beaker are added 150 mL of pure water at 70° C. and 2 mL of 1:1 sulfuric acid (i.e., a sulfuric acid aqueous solution obtained by mixing concentrated sulfuric acid and water at a volume ratio of 1/1). Thereafter, the opening of the beaker is covered with a watch glass, and a solution in the beaker is stirred in a water bath at 70° C.±2° C. for 1 hour to oxidize the sample. At this occasion, $KMnO_4$ is made to be present excessively. Since the solution has unreacted $KMnO_4$, whether or not the liquid color is purple is verified. After completion of the oxidation, filtration is performed with a filter paper to collect an entire amount of a filtrate. Then, an excessive amount of a sodium oxalate ($Na_2C_2O_4$) aqueous solution having a known concentration is added to $KMnO_4$ present in the filtrate, and thereafter the solution is heated to a liquid temperature of 70° C. and stirred. Whether or not the solution becomes colorless and transparent is verified, and then 2 mL of 1:1 sulfuric acid is added thereto. Further, the stirring is made to continue while keeping the liquid temperature at 70° C.±2° C., and titration is carried out using a $KMnO_4$ aqueous solution having a known concentration. The titration with $KMnO_4$ causes its liquid color to become a slight light pink. The termination point is set to where the slight light pink continues for about 30 seconds. By determining a total amount of $KMnO_4$ and a total amount of $Na_2C_2O_4$, an amount of $KMnO_4$ consumed for oxidizing the sample is to be estimated. By using this $KMnO_4$ amount, the $(n_0-n)$ is calculated. Based on this value, the rate of reduction is determined.

For example, a rate of reduction of the oxide catalyst after completion of calcination is determined as follows.

First, about 200 mg of the catalyst ground with an agate-made mortar is weighed precisely and added to a beaker. To the beaker are added 150 mL of pure water at 95° C. and 4 mL of 1:1 sulfuric acid (i.e., a sulfuric acid aqueous solution obtained by mixing concentrated sulfuric acid and water at a volume ratio of 1/1). Next, stirring is performed while keeping the liquid temperature at 95° C.±2° C., and titration is carried out using a $KMnO_4$ aqueous solution having a known concentration. At this occasion, dropwise addition of $KMnO_4$ causes its liquid color to become purple temporarily. In order not to have the purple color continue for 30 seconds or more, a small amount of $KMnO_4$ is slowly added dropwise. In addition, evaporation of water causes a liquid volume to decrease, so that pure water at 95° C. is additionally added at any time so as to keep the liquid volume constant. The titration with $KMnO_4$ causes its liquid color to become a slight light pink. The termination point is set to where the slight light pink continues for about 30 seconds. In this manner, an amount of $KMnO_4$ consumed for oxidizing the sample is to be estimated. By using this $KMnO_4$ amount, the $(n_0-n)$ is calculated. Based on this value, the rate of reduction is determined.

In addition to the above measurement procedure, with regard to either of the catalyst precursor before completion of calcination and the oxide catalyst after completion of calcination, a rate of reduction can be determined as follows.

Specifically, under conditions of there being no volatilization or escape of constituent elements of a sample and under conditions of an oxygen-containing atmosphere, a sample is heated to a temperature higher than a calcination temperature at which the catalyst precursor or catalyst is calcined. Accordingly, the sample is completely oxidized by oxygen. Then, increased mass (i.e., an amount of bound oxygen) is to be estimated. By using this amount, the value of $(n_0-n)$ is calculated. Finally, based on this value, the rate of reduction is determined.

First, a temperature of a dried catalyst precursor continuously or stepwisely rises from a temperature lower than 400° C. to a temperature range between 550 and 700° C. Calcination is carried out under such a calcination condition. Then, it is preferable to adjust the calcination condition so as to achieve 8 to 12% of a rate of reduction of the catalyst precursor during the calcination when the heating temperature reaches 400° C.

In general, the rate of reduction of the oxide catalyst is affected by an amount of an organic component such as oxalic acid included in the dried powder, an amount of an ammonia residue derived from raw material ammonium salts, and a rate of temperature rise at the initiation of calcination. When calcination is carried out under an inert gas atmosphere, the rate of reduction is affected by a volume of inert gas. When calcination is carried out under an air atmosphere, the rate of reduction is affected by its temperature and time.

When a catalyst constituent element in the dried catalyst precursor has an approximately maximum oxidation number, only reduction should be carried out during the calcination step so as to keep a rate of reduction of the oxide catalyst within a desired range. This is industrially convenient. It is preferable to maintain the calcination atmosphere under an inert gas atmosphere because the rate of reduction is readily adjustable.

In order to keep the rate of reduction of the oxide catalyst at 8 to 12%, there is a following procedure. For example, a temperature rise is initiated at a temperature lower than 400° C. at the time of calcination. Next, an oxalic acid residue and ammonium residue included in the dried powder are degraded. Then, generation of gas is almost completely terminated to achieve 8 to 12% of a rate of reduction of the catalyst precursor during the calcination when the heating temperature reaches 400° C.

The specific surface area of the catalyst is affected by a final calcination (heating) temperature and time and a supporting amount of a carrier when the catalyst is supported on the carrier such as silica. However, the specific surface area is most affected by the final calcination temperature and the rate of reduction when the heating temperature reaches 400° C., in particular. In view of such a situation, the final calcination temperature is preferably 550° C. to 700° C., and the calcination time at that temperature is preferably 0.5 hour to 20 hours. As the final calcination temperature increases or as the calcination time increases, the specific surface area tends to become smaller.

In addition, when the heating temperature reaches 400° C., the rate of reduction may be within 8 to 12%, which is likely to be able to prevent an excessive decrease or increase in the specific surface area of the catalyst.

For example, in order to keep the specific surface area of the catalyst at 5 to 30 $m^2/g$, it is preferable to set the rate of reduction when the heating temperature reaches 400° C. to a range between 8 and 12% and it is also preferable to have a final calcination temperature of 550° C. to 700° C.

When the rate of reduction of the catalyst precursor during calcination is determined, a sample may be collected from a calcination apparatus at that temperature. In the case of a high temperature, contact with air may cause oxidation and a change in the rate of reduction. Hence, the catalyst precursor obtained by collecting from the calcination apparatus after cooling to room temperature may be selected as a representative sample.

Examples of a process for regulating a rate of reduction within a desired range when a heating temperature reaches 400° C. specifically include a process for adjusting a calcination temperature during pre-stage calcination, a process for adding an oxidizing component such as oxygen to an atmosphere during calcination, and a process for adding a reducing component to an atmosphere during calcination. In addition, among these processes, two or more of the processes may be combined.

The process for adjusting a calcination temperature during pre-stage calcination (hereinafter, referred to as a "pre-stage calcination temperature") is a process including the step of changing a pre-stage calcination temperature, so that a rate of reduction of a catalyst precursor is adjusted when a heating temperature reaches 400° C. Usually, as the pre-stage calcination temperature decreases, the rate of reduction tends to become lower. As the pre-stage calcination temperature increases, the rate of reduction tends to become higher. Therefore, changes in the pre-stage calcination temperature can regulate the rate of reduction.

The process for adding an oxidizing component such as oxygen to an atmosphere during calcination is a process in which a rate of reduction of a catalyst precursor can be decreased when a heating temperature reaches 400° C. As used herein, the term "during calcination" may refer to pre-stage calcination, main calcination, or both the calcination.

The oxidizing component which is added to an atmosphere during calcination is an oxidizing component in inert gas supplied to a calcination apparatus. The additive amount of the oxidizing component can be controlled by its concentration in the inert gas supplied to the calcination apparatus. Addition of this oxidizing component can regulate a rate of reduction of a catalyst precursor when a heating temperature reaches 400° C. When the oxidizing component is oxygen, air (or an air-containing inert gas) is fed into the calcination apparatus, so that oxygen in the air can be utilized as an oxidizing component.

The process for adding a reducing component to an atmosphere during calcination is a process in which a rate of reduction of a catalyst precursor can be increased when a heating temperature reaches 400° C. As used herein, the term "during calcination" may refer to pre-stage calcination, main calcination, or both the calcination.

The reducing component which is added to an atmosphere during calcination is a reducing component in inert gas supplied to a calcination apparatus. The additive amount of the reducing component can be controlled by its concentration in the inert gas supplied to the calcination apparatus. Addition of this reducing component can regulate a rate of reduction of a catalyst precursor when a heating temperature reaches 400° C. As the reducing component, ammonia, for example, can be used.

By the way, when the rate of reduction of the catalyst precursor when the heating temperature reaches 400° C. is not a desired rate of reduction, a total amount of the necessary oxidizing or reducing component is calculated by using a difference between the actual rate of reduction and the desired rate of reduction. Then, either component can be added to the atmosphere during calcination.

When the catalyst is used in a fluidized bed, sufficient strength is required. Consequently, the oxide catalyst is preferably supported on silica. When converted to an $SiO_2$ equivalent, the oxide catalyst is supported on silica at preferably 10 to 80% by mass, more preferably 20 to 60% by mass, and still more preferably 30 to 55% by mass per total mass of the oxide catalyst (i.e., an oxide of catalyst constituent elements which serve as main catalysts) and the silica. From the viewpoints of strength, prevention of powderization, and easy and stable operation at the time of using the catalyst and a view point of decreasing compensation of the lost catalyst, the amount of the silica of a carrier is preferably 10% by mass or more per total mass of the oxide catalyst and the silica. From the viewpoint of achieving a sufficient catalytic activity, the amount of the silica is preferably 80% by mass or less per total mass of the oxide catalyst and the silica. When the catalyst is used in a fluidized bed, in particular, having a silica amount at 80% by mass or less renders a specific gravity of the silica-supported catalyst (the oxide catalyst+the silica carrier) appropriate. This is likely to cause a better fluidized state.

[Process for Producing an Unsaturated Acid and an Unsaturated Nitrile]

An oxide catalyst obtained using a production process according to an embodiment of the present invention is brought into contact with an alkane such as propane and isobutane or an alkene such as propylene and isobutene. Then, these compounds can be reacted with molecular oxygen in a gas phase (i.e., a gas phase catalytic oxidation reaction) to produce corresponding unsaturated carboxylic acid (e.g., acrylic acid or methacrylic acid). In addition, this oxide catalyst is brought into contact with an alkane such as propane and isobutane or an alkene such as propylene and isobutene. Then, these compounds can be reacted with ammonia and molecular oxygen in a gas phase (i.e., a gas phase catalytic ammoxidation reaction) to produce corresponding unsaturated nitrile (e.g., acrylonitrile or methacrylonitrile).

The supply feedstock of ammonia and, propane, isobutane, propylene, or isobutene is not necessarily high purity. So, an industrial-grade gas can be used. An oxygen source can employ air, pure oxygen, or pure oxygen-rich air. Furthermore, helium, neon, argon, carbon dioxide, water vapor, or nitrogen, etc., may be supplied as diluent gas.

In the case of the ammoxidation reaction, a molar ratio of ammonia to be supplied to a reaction system to, for example, propane or isobutane is preferably 0.3 to 1.5 and more preferably 0.8 to 1.2. In either case of the oxidation and ammoxidation reactions, a molar ratio of molecular oxygen to be supplied to a reaction system to, for example, propane or isobutane is preferably 0.1 to 6 and more preferably 0.1 to 4.

In addition, in either case of the oxidation and ammoxidation reactions, the reaction pressure is preferably 0.5 to 5 atm and more preferably 1 to 3 atm. The reaction temperature is preferably 350° C. to 500° C. and more preferably 380° C. to 470° C. The contact time is preferably 0.1 to 10 (sec·g/cc) and more preferably 0.5 to 5 (sec·g/cc). The contact time is defined by the following equation:

$$\text{Contact time (sec·g/cc)}=(W/F)\times 273/(273+T)\times P,$$

wherein W=catalyst mass (g); F=a flow rate of the raw material mixed gas (Ncc/sec) at a standard condition (0° C., 1 atm); T=a reaction temperature (° C.); and P=a reaction pressure (atm).

The propane conversion and the acrylonitrile yield each follow the definitions below.

Propane conversion (%)=(Mole number of propane reacted)/(Mole number of propane supplied)×100.

Acrylonitrile yield (%)=(Mole number of acrylonitrile generated)/(Mole number of propane supplied)×100.

The reaction process can employ conventional processes such as a fixed bed, a fluidized bed, and a moving bed. However, the fluidized bed reaction is preferable because: the reaction heat can be easily removed; the temperature of the catalyst layer can be almost uniformly maintained; the catalyst can be extracted from a reactor during operation; the catalyst can be further added; and others.

Also, in the above-described embodiments, inert gas is fed into the sealed chamber and the specific space. However, inert gas may not be supplied to the sealed chamber and the specific space. In an embodiment of the present invention, a sealed chamber is provided between the specific space and the outside. If outside air infiltrates into the specific space, the air must pass through the sealed chamber. Therefore, the infiltration amount of the air can be decreased when compared to the case without the sealed chamber.

When the catalyst precursor is calcined using a calcination apparatus according to an embodiment of the present invention, the insides of the calcination tube and the specific space can be kept under a desired atmosphere for a long period of time. Therefore, a catalyst used for producing a high yield of a product of interest can be continuously produced.

EXAMPLES

Hereinafter, the present embodiment will be described in more detail by way of Examples and Comparative Examples, but the present embodiment is not limited to these Examples.

(Preparation of a Niobium Raw Material Liquid)

A niobium raw material liquid was prepared by the following method. 76.33 kg of niobic acid containing 80.2% by mass in terms of $Nb_2O_5$ and 29.02 g of oxalic acid dihydrate [$H_2C_2O_4 \cdot 2H_2O$] were mixed in 500 kg of water. The molar ratio of the oxalic acid/niobium charged was 5.0, and the concentration of niobium charged was 0.532 (mol-Nb/kg-liquid).

The liquid was heated and stirred at 95° C. for 1 hour to thereby obtain an aqueous solution in which a niobium compound was dissolved. The aqueous solution was left to stand, and cooled with ice; and a solid was filtered out by suction filtration to thereby obtain a homogeneous niobium compound aqueous solution. The same operation was repeated several times; and the niobium compound aqueous solutions obtained were unified to thereby make a niobium raw material liquid. The molar ratio of oxalic acid/niobium of the niobium raw material liquid was 2.70 by the following analysis.

10 g of the niobium raw material liquid was precisely weighed in a crucible, dried at 95° C. over night, and thermally treated at 600° C. for 1 hour to thereby obtain 0.7868 g of $Nb_2O_5$. From the result, the niobium concentration was 0.592 (mol-Nb/kg-liquid).

3 g of the niobium raw material liquid was precisely weighed in a 300-mL glass beaker; and 200 mL of hot water at about 80° C. was added, and 10 mL of a 1:1 sulfuric acid was then added. The solution obtained was titrated at a solution temperature being held at 70° C. under stirring on a hot stirrer by using a 1/4-N $KMnO_4$. A point at which a faint light peach color due to the $KMnO_4$ continued for about 30 sec or longer was defined as an end point. The concentration of oxalic acid was calculated by the following formula from the titration amount, and was revealed to be 1.60 (mol-oxalic acid/kg-liquid).

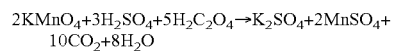

The preparation step for the niobium raw material liquid was suitably repeated and the niobium raw material liquids obtained were used as niobium raw material liquids in the following productions of oxide catalysts.

Example 1

A silica-supported catalyst whose composition formula was represented by $Mo_1V_{0.24}Nb_{0.095}Sb_{0.27}W_{0.031}Ce_{0.005}O_n$/45 mass %-$SiO_2$ was produced as follows.

(Preparation of a Raw Material Mixture)

32.5 kg of ammonium heptamolybdate [$(NH_4)_6Mo_7O_{24} \cdot 4H_2O$], 5.13 kg of ammonium metavanadate [$NH_4VO_3$], 7.23 kg of diantimony trioxide [$Sb_2O_3$], and 0.404 kg of cerium nitrate [$Ce(NO_3)_3 \cdot 6H_2O$] were added to 133.4 kg of water, and heated under stirring at 95° C. for 1 hour to thereby obtain an aqueous mixed liquid A-1.

3.94 kg of a hydrogen peroxide solution containing 30% by mass of $H_2O_2$ was added to 29.3 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 58.60 kg of a silica sol containing 30.4% by mass in terms of $SiO_2$ was thereafter added. Then, 8.39 kg of a hydrogen peroxide solution containing 30% by mass of $H_2O_2$ was added, and stirred and mixed at 50° C. for 1 hour; and the aqueous mixed liquid B-1 was then added. A liquid in which 13.8 kg of a fumed silica was dispersed in 186.8 kg of water, and 2.62 kg of ammonium metatungstate containing 50.2% by mass of $WO_3$ were further sequentially added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.

(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.

(Calcination)

A calcination apparatus was prepared which had: a calcination tube 1 having open ends at both terminals thereof; a pair of hoods 2 (which were each of a cylindrical type opening at one terminal, and composed of a material of SUS, and had a size of a length of 450 mm for the open end side to charge a powder through (hereinafter, simply referred to as "powder inlet side") and a size of a length of 1,000 mm for the open end side to discharge a powder through (hereinafter, simply referred to as "powder outlet side", and both had an internal diameter of 960 mm) respectively covering the open ends of the calcination tube 1; and a pair of V rings 3 (which were each of a V-shape having separated cross-sectional shapes (see FIG. 3(F)), and composed of a material of Viton rubber, and each had a size of an inner diameter of 750 mm, a width w of 140 mm, a height d2 of 40 mm and a wall thickness d1 of 8 mm, into each sealed chamber of which a nitrogen gas was introduced (the flow volume was 60 NL/min at the powder inlet side and the powder outlet side), and each had a sealing support whose size was a width of 140 mm, a width of a protrusion of 10 mm and a height (excluding the protrusion) of 80 mm, and whose material was SUS) respectively sealing gaps between the calcination tube 1 and the hoods 2, wherein the hood 2 of the open end side through which a powder was charged of the calcination tube 1 was heated at 130° C. from the outside; the hoods 2 had, on both terminals of the powder inlet side and the powder outlet side of the calcination tube 1, a plurality of inert gas inlets 26 arranged as in FIG. 6 and a plurality of inert gas inlets 21 arranged as in FIG. 9; and an outlet was installed in the hood 2 of the open end side through which a powder is charged so that the front end of a nozzle of the outlet was made flush with the terminal surface of the open end of the calcination tube 1, and which calcination apparatus had the same other structures as those shown in FIG. 9. The dried catalyst precursor obtained as described above was circulated at a rate of 28 kg/hr and pre-stage-calcined in the calcination apparatus using a SUS cylindrical calcination tube 1 which had an inner diameter of 650 mm, a length of 5,500 mm and a wall thickness of 20 mm, which was installed with seven weir plates having a height of 135 mm so that the length of a section of a heating furnace was divided into eight equal sections, and in which while a nitrogen gas was supplied at 440 NL/min from the inert gas inlets 21 of the powder inlet side, and a nitrogen gas was supplied at 330 NL/min from the inert gas inlets 21 of the powder outlet side, the temperature of the heating furnace was regulated so as to have a temperature profile of being raised up to 370° C. over about 5 hours and held at 370° C. for 3 hours in the state of the calcination tube 1 being rotated at 4 rpm, to thereby obtain a pre-stage calcination powder.

Then, the pre-stage calcination powder was circulated at a rate of 28 kg/hr in the calcination apparatus using another SUS calcination tube 1 which had an inner diameter of 650 mm, a length of 5,500 mm and a wall thickness of 20 mm, which was installed with seven weir plates having a height of 160 mm so that the length of a section of a heating furnace was divided into eight equal sections, and which was being rotated at 4 rpm. At this time, while a portion of the powder inlet side and a portion of the powder outlet side (either portion was a portion not being covered with the heating furnace) of the calcination tube 1 were each hammered once at every 5 sec from a height of 250 mm above the calcination tube 1 in the direction perpendicular to the rotation axis by a hammering device equipped with a hammer of 16 kg in mass with a SUS hammering tip end, and while a nitrogen gas was being supplied at 350 NL/min from each of the powder inlet side and the powder outlet side and the calcination tube 1 was in the rotation state at 4 rpm, the temperature of the heating furnace was regulated so as to have a temperature profile of being raised up to 675° C. at 2° C./min, held at 675° C. for 2 hours for calcination, and descended at 1° C./min, to thereby carry out a main calcination of the pre-stage calcination powder to thereby obtain an oxide catalyst. During the main calcination, no decrease in the calcination temperature occurred and the oxide catalyst could be obtained at a stable rate. The vibration acceleration was measured by a vibrometer (MD-220, made by Asahi Kasei Technosystem Co., Ltd.), and was 55 m/s² and f was 2.08. The conditions of pressure, oxygen concentrations and the like in the specific space at this time were as shown in Table 1 for both the pre-stage calcination and the main calcination.

(Evaluation of the Catalyst Performance)

45 g of the oxide catalyst obtained after 48 hours (2 days) from the calcination start was packed in a Vicol-glass fluidized-bed reaction tube having an inner diameter of 25 mm; and a mixed gas of propane:ammonia:oxygen:helium=1:0.85:3.0:11 in molar ratio was passed therethrough at a contact time of 3.0 (sec·g/cc) at a reaction temperature of 440° C. and under normal pressure of the reaction pressure, and the reaction result was confirmed. The reaction results were similarly confirmed on oxide catalysts obtained after 15 days and 40 days from the calcination start. The reaction results in the case of using the oxide catalysts after 2 days, 15 days and 40 days from the start of the continuous calcination are shown in Table 1.

Example 2

A silica-supported catalyst whose composition formula was represented by $Mo_1V_{0.24}Nb_{0.095}Sb_{0.27}W_{0.031}Ce_{0.005}O_n$/45 mass %-$SiO_2$ was produced as follows.

(Preparation of a Raw Material Mixture)

A raw material mixture was prepared as in Example 1, except for preparing about 640 kg of the total of the raw material mixture by repeating eight times the present step in order to carry out a step of "preparation of a dried catalyst precursor" and a "calcination" step in a continuous system.

(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.

(Calcination)

The same calcination apparatus as in Example 1 was used, except that the calcination apparatus had: a calcination tube 1 described below; a pair of hoods 2 (which were each of a cylindrical type opening at one terminal, and composed of a material of SUS, and had a size of a length of 150 mm for the powder inlet side and a length of 320 mm for the powder outlet side, and both had an internal diameter of 340 mm) respectively covering the open ends of the calcination tube 1; and a pair of V rings 3 (which were each of a V-shape having separated cross-sectional shapes (see FIG. 3(F)), and composed of a material of Viton rubber, and each had a size of an inner diameter of 250 mm, a width w of 40 mm, a height d2 of 7 mm and a wall thickness d1 of 2 mm, into each sealed chamber of which a nitrogen gas was introduced (the flow volume was 1.2 NL/min at the powder inlet side and the powder outlet side), and each had a sealing support whose size was a width of 45 mm, a width of a protrusion of 9 mm and a height (excluding the protrusion) of 30 mm, and whose material was SUS) respectively sealing gaps between the calcination tube 1 and the hoods 2. The dried catalyst precursor obtained was circulated at a rate of 540 g/hr and pre-stage-calcined in the SUS cylindrical calcination tube which had an inner diameter of 200 mm, a length of 1,500 mm and a wall thickness of 7 mm, which was installed with seven weir plates having a height of 33.8 mm so that the length of a section of a heating furnace was divided into eight equal sections, and in which while a nitrogen gas was supplied at 8 NL/min from the powder inlet side, and a nitrogen gas was supplied at 8 NL/min from the powder outlet side, the temperature of the heating furnace was regulated so as to have a temperature profile of being raised up to 370° C. over about 5 hours and held at 370° C. for 3 hours in the state of the calcination tube 1 being rotated at 4 rpm, to thereby obtain a pre-stage calcination powder.

Then, the pre-stage calcination powder was circulated at a rate of 540 g/hr in the calcination apparatus using another SUS calcination tube 1 which had an inner diameter of 200 mm, a length of 1,500 mm and a wall thickness of 7 mm, which was installed with seven well plates having a height of 42 mm so that the length of a section of a heating furnace was divided into eight equal sections, and which was being rotated at 4 rpm. At this time, while a portion which was a portion not being covered with the heating furnace of the powder inlet section of the calcination tube 1 was hammered once at every 5 sec from a height of 35 mm above the calcination tube 1 in the direction perpendicular to the rotation axis by a hammering device equipped with a hammer of 3 kg in mass with a SUS hammering tip end, and while a nitrogen gas was being supplied at 6.8 NL/min from each of the powder inlet side and the powder outlet side and the calcination tube 1 was in the rotation state at 4 rpm, the temperature of the heating furnace was regulated so as to have a temperature profile of being raised up to 675° C. at 2° C./min, held at 675° C. for 2 hours for calcination, and descended at 1° C./min, to thereby carry out a main calcination of the pre-stage calcination powder to thereby obtain an oxide catalyst. During the main calcination, no decrease in the calcination temperature occurred and the oxide catalyst could be obtained at a stable rate. The vibration acceleration was measured by a vibrometer (MD-220, made by Asahi Kasei Technosystem Co., Ltd.), and was 60 m/s² and f was 2.27. The conditions of pressure, oxygen concentrations and the like in the specific space at this time were as shown in Table 1 for both the pre-stage calcination and the main calcination.

(Evaluation of the Catalyst Performance)

45 g of the oxide catalyst obtained after 48 hours from the calcination start was packed in a Vicol-glass fluidized-bed reaction tube having an inner diameter of 25 mm; and a mixed gas of propane:ammonia:oxygen:helium=1:0.85:3.0:11 in molar ratio was passed therethrough at a contact time of 3.0 (sec·g/cc) at a reaction temperature of 440° C. and under normal pressure of the reaction pressure. The reaction results after 2 days and 40 days from the start of the continuous calcination are shown in Table 1.

Example 3

A catalyst was prepared as in Example 1, except for making the pressure P1 in the specific space to be 0 mmH$_2$O and the pressure difference P2 between the specific space and the sealed chamber to be 60 mmH$_2$O, and the catalyst performance was evaluated as in Example 1. The results are shown in Table 1.

Example 4

A catalyst was prepared as in Example 1, except for making the pressure P1 in the specific space to be 0 mmH$_2$O and the pressure difference P2 between the specific space and the sealed chamber to be 40 mm H$_2$O, and the catalyst performance was evaluated as in Example 1. The results are shown in Table 1.

Example 5

A catalyst was prepared as in Example 1, except for making the pressure P1 in the specific space to be 0 mmH$_2$O and the pressure difference P2 between the specific space and the sealed chamber to be 0 mmH$_2$O, and the catalyst performance was evaluated as in Example 1. The results are shown in Table 1.

Comparative Example 1

A catalyst was prepared as in Example 2, except for equipping O rings (which had a material of Viton rubber, and a size of an inner diameter of 645 mm) in place of the V rings 3, and making the inner diameter of hoods 2 to be 700 mm and the pressure P1 in the specific space to be 50 mmH$_2$O, and the catalyst performance was evaluated as in Example 2. The results are shown in Table 1.

Comparative Example 2

A catalyst was prepared as in Example 1, except for equipping oil seals in place of the V rings 3, and making the pressure P1 in the specific space to be 0 mmH$_2$O, and the catalyst performance was evaluated as in Example 1. The results are shown in Table 1.

Comparative Example 3

A catalyst was prepared as in Example 1, except for equipping oil seals in place of the V rings 3, and making the pressure P1 in the specific space to be 50 mmH$_2$O, and the catalyst performance was evaluated as in Example 1. The results are shown in Table 1.

Comparative Example 4

A catalyst was prepared as in Example 2, except for equipping oil seals in place of the V rings 3, and making the pressure P1 in the specific space to be 100 mmH$_2$O, and the catalyst performance was evaluated as in Example 2. The oxygen concentration was measured on the 15th day after the start of the continuous calcination, and was revealed to rise largely as compared with that after the calcination start. The continuous calcination was judged to be impossible, and the calcination apparatus was dismantled and checked; since the oil seals were proved to be worn, the oil seals must have been replaced. The results are shown in Table 1.

Example 6

A catalyst was prepared as in Example 2, except for equipping lip seals 3 (which were each of a U-shape having separated cross-sectional shapes (see FIG. 3(E)), and composed of a material of Viton rubber, and each had a size of an inner diameter of 230 mm, a width w of 40 mm, a height d2 of 7 mm and a wall thickness of 3 mm, into each sealed chamber of which a nitrogen gas was introduced (the flow volume was 1.2 NL/min at each of the powder inlet side and the powder outlet side), and each had a sealing support whose size was a width of 45 mm, a width of a protrusion of 9 mm and a height (excluding the protrusion) of 30 mm, and whose material was SUS) in place of the V rings 3, and making the pressure P1 in the specific space to be 50 mmH$_2$O and the pressure difference P2 between the specific space and the sealed chamber to be 40 mmH$_2$O, and the catalyst performance was evaluated as in Example 2. The results are shown in Table 1.

Example 7

A catalyst was prepared as in Example 1, except for equipping lip seals 3 (which were each of a U-shape having separated cross-sectional shapes (see FIG. 3(E)), and composed of a material of Viton rubber, and each had a size of an inner diameter of 730 mm, a width w of 90 mm, a height d2 of 40 mm and a wall thickness of 6 mm, into each sealed chamber of which a nitrogen gas was introduced (the flow volume was 60 NL/min at each of the powder inlet side and the powder outlet side), and each had a sealing support whose size was a width of 140 mm, a width of a protrusion of 10 mm and a height (excluding the protrusion) of 80 mm, and whose material was SUS) in place of the V rings 3, and making the pressure P1 in the specific space to be 40 mmH$_2$O and the pressure difference P2 between the specific space and the sealed chamber to be 20 mmH$_2$O, and the catalyst performance was evaluated as in Example 1. The results are shown in Table 1.

Example 8

A silica-supported catalyst whose composition formula was represented by Mo$_1$V$_{0.24}$Nb$_{0.095}$Sb$_{0.27}$O$_n$/45 mass %-SiO$_2$ was produced as follows.
(Preparation of a Raw Material Mixture)
33.7 kg of ammonium heptamolybdate [(NH$_4$)$_6$Mo$_7$O$_{24}$.4H$_2$O], 5.32 kg of ammonium metavanadate [NH$_4$VO$_3$], and 7.49 kg of diantimony trioxide [Sb$_2$O$_3$] were added to 138.3 kg of water, and heated under stirring at 95° C. for 1 hour to thereby obtain an aqueous mixed liquid A-1.

4.08 kg of a hydrogen peroxide solution containing 30% by mass of H$_2$O$_2$ was added to 30.4 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 58.60 kg of a silica sol containing 34.0% by mass in terms of SiO$_2$ was thereafter added. Then, 8.70 kg of a hydrogen peroxide solution containing 30% by mass of H$_2$O$_2$ was added, and stirred and mixed at 50° C. for 1 hour; and the aqueous mixed liquid B-1 was then added. A liquid in which 13.8 kg of a fumed silica was dispersed in 186.8 kg of water was further added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.
(Preparation of a Dried Catalyst Precursor)
The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)
The calcination was carried out as in Example 1 to obtain a catalyst.
(Evaluation of the Catalyst Performance)
The evaluation was carried out as in Example 1. The results are shown in Table 2.

Example 9

A silica-supported catalyst whose composition formula was represented by Mo$_1$V$_{0.24}$Nb$_{0.095}$Sb$_{0.27}$W$_{0.03}$Mn$_{0.002}$/45 mass %-SiO$_2$ was produced as follows.
(Preparation of a Raw Material Mixture)
32.6 kg of ammonium heptamolybdate [(NH$_4$)$_6$Mo$_7$O$_{24}$.4H$_2$O], 5.15 kg of ammonium metavanadate [NH$_4$VO$_3$], and 7.26 kg of diantimony trioxide [Sb$_2$O$_3$] were added to 154.6 kg of water, and heated under stirring at 95° C. for 1 hour to thereby obtain an aqueous mixed liquid A-1.

3.95 kg of a hydrogen peroxide solution containing 30% by mass of H$_2$O$_2$ was added to 29.4 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 58.60 kg of a silica sol containing 34.0% by mass in terms of SiO$_2$ was thereafter added. Then, 8.42 kg of a hydrogen peroxide solution containing 30% by mass of H$_2$O$_2$ was added, and stirred and mixed at 50° C. for 1 hour; and the aqueous mixed liquid B-1 was then added.

A liquid in which 13.8 kg of a fumed silica was dispersed in 186.8 kg of water, and 2.55 kg of ammonium metatungstate containing 50% by mass of WO$_3$ and 0.105 kg of manganese nitrate [Mn(NO$_3$)$_2$.6H$_2$O] were further sequentially added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.
(Preparation of a Dried Catalyst Precursor)
The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)
The calcination was carried out as in Example 1, except for the condition shown in Table 1, to obtain a catalyst.
(Evaluation of the Catalyst Performance)
The evaluation was carried out as in Example 1. The results are shown in Table 2.

Example 10

A silica-supported catalyst whose composition formula was represented by Mo$_1$V$_{0.24}$Nb$_{0.095}$Sb$_{0.27}$B$_{0.05}$/45 mass %-SiO$_2$ was produced as follows.
(Preparation of a Raw Material Mixture)
33.4 kg of ammonium heptamolybdate [(NH$_4$)$_6$Mo$_7$O$_{24}$.4H$_2$O], 5.28 kg of ammonium metavanadate [NH$_4$VO$_3$], and 7.43 kg of diantimony trioxide [Sb$_2$O$_3$] were added to 163.6 kg of water, and heated under stirring at 95° C. for 1 hour to thereby obtain an aqueous mixed liquid A-1.

4.05 kg of a hydrogen peroxide solution containing 30% by mass of H$_2$O$_2$ was added to 30.2 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 58.60 kg of a silica sol containing 34.0% by mass in terms of SiO$_2$ was thereafter added. Then, 8.63 kg of a hydrogen peroxide solution containing 30% by mass of H$_2$O$_2$ was added, and stirred and mixed at 50° C. for 1 hour; and the aqueous mixed liquid B-1 was then added. A liquid in which 13.8 kg of a fumed silica was dispersed in 186.8 kg of water, and 0.586 kg of boric acid [H$_3$BO$_3$] were further sequentially added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.

(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.

(Calcination)

The calcination was carried out as in Example 1, except for the condition shown in Table 1, to obtain a catalyst.

(Evaluation of the Catalyst Performance)

The evaluation was carried out as in Example 1. The results are shown in Table 2.

Example 11

A silica-supported catalyst whose composition formula was represented by $Mo_1V_{0.24}Nb_{0.095}Sb_{0.27}Al_{0.01}/45$ mass $\%$-$SiO_2$ was produced as follows.

(Preparation of a Raw Material Mixture)

33.6 kg of ammonium heptamolybdate [$(NH_4)_6Mo_7O_{24}.4H_2O$], 5.31 kg of ammonium metavanadate [$NH_4VO_3$], and 7.47 kg of diantimony trioxide [$Sb_2O_3$] were added to 164.6 kg of water, and heated under stirring at 95° C. for 1 hour to thereby obtain an aqueous mixed liquid A-1.

4.07 kg of a hydrogen peroxide solution containing 30% by mass of $H_2O_2$ was added to 30.3 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 58.60 kg of a silica sol containing 34.0% by mass in terms of $SiO_2$ was thereafter added. Then, 8.68 kg of a hydrogen peroxide solution containing 30% by mass of $H_2O_2$ was added, and stirred and mixed at 50° C. for 1 hour; and the aqueous mixed liquid B-1 was then added. A liquid in which 13.8 kg of a fumed silica was dispersed in 186.8 kg of water, and 0.096 kg of aluminum oxide [$Al_2O_3$] were further sequentially added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.

(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.

(Calcination)

The calcination was carried out as in Example 1, except for the condition shown in Table 1, to obtain a catalyst.

(Evaluation of the Catalyst Performance)

The evaluation was carried out as in Example 1. The results are shown in Table 2.

Example 12

A silica-supported catalyst whose composition formula was represented by $Mo_1V_{0.24}Nb_{0.095}Sb_{0.27}W_{0.03}Ti_{0.008}/45$ mass $\%$-$SiO_2$ was produced as follows.

(Preparation of a Raw Material Mixture)

33.6 kg of ammonium heptamolybdate [$(NH_4)_6Mo_7O_{24}.4H_2O$], 5.31 kg of ammonium metavanadate [$NH_4VO_3$], and 7.47 kg of diantimony trioxide [$Sb_2O_3$] were added to 164.5 kg of water, and heated under stirring at 95° C. for 1 hour to thereby obtain an aqueous mixed liquid A-1.

4.07 kg of a hydrogen peroxide solution containing 30% by mass of $H_2O_2$ was added to 30.3 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 58.60 kg of a silica sol containing 34.0% by mass in terms of $SiO_2$ was thereafter added. Then, 8.67 kg of a hydrogen peroxide solution containing 30% by mass of $H_2O_2$ was added, and stirred and mixed at 50° C. for 1 hour; and the aqueous mixed liquid B-1 was then added. A liquid in which 13.8 kg of a fumed silica was dispersed in 186.8 kg of water, and 0.121 kg of titanium oxide [$TiO_2$] were further sequentially added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.

(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.

(Calcination)

The calcination was carried out as in Example 1, except for the condition shown in Table 1, to obtain a catalyst.

(Evaluation of the Catalyst Performance)

The evaluation was carried out as in Example 1. The results are shown in Table 2.

Example 13

A silica-supported catalyst whose composition formula was represented by $Mo_1V_{0.24}Nb_{0.095}Sb_{0.27}Ta_{0.01}/45$ mass $\%$-$SiO_2$ was produced as follows.

(Preparation of a Raw Material Mixture)

33.3 kg of ammonium heptamolybdate [$(NR_4)_6Mo_7O_{24}.4H_2O$], 5.27 kg of ammonium metavanadate [$NH_4VO_3$], and 7.42 kg of diantimony trioxide [$Sb_2O_3$] were added to 158.0 kg of water, and heated under stirring at 95° C. for 1 hour to thereby obtain an aqueous mixed liquid A-1.

4.04 kg of a hydrogen peroxide solution containing 30% by mass of $H_2O_2$ was added to 30.1 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 58.60 kg of a silica sol containing 34.0% by mass in terms of $SiO_2$ was thereafter added. Then, 8.61 kg of a hydrogen peroxide solution containing 30% by mass of $H_2O_2$ was added, and stirred and mixed at 50° C. for 1 hour; and the aqueous mixed liquid B-1 was then added. A liquid in which 13.8 kg of a fumed silica was dispersed in 186.8 kg of water, and 0.473 kg of tantalic acid were further sequentially added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.
(Preparation of a Dried Catalyst Precursor)
The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)
The calcination was carried out as in Example 1, except for the condition shown in Table 1, to obtain a catalyst.
(Evaluation of the Catalyst Performance)
The evaluation was carried out as in Example 1. The results are shown in Table 2.

Example 14

A silica-supported catalyst whose composition formula was represented by $Mo_1V_{0.24}Nb_{0.095}Sb_{0.27}Ce_{0.004}Bi_{0.02}/45$ mass %-$SiO_2$ was produced as follows.
(Preparation of a Raw Material Mixture)
32.9 kg of ammonium heptamolybdate $[(NH_4)_6Mo_7O_{24}.4H_2O]$, 5.20 kg of ammonium metavanadate $[NH_4VO_3]$, 7.31 kg of diantimony trioxide $[Sb_2O_3]$, and 0.327 kg of cerium nitrate $[Ce(NO_3)_3.6H_2O]$ were added to 161.0 kg of water, and heated under stirring at 95° C. for 1 hour to thereby obtain an aqueous mixed liquid A-1.
3.98 kg of a hydrogen peroxide solution containing 30% by mass of $H_2O_2$ was added to 29.7 kg of the niobium raw material liquid. The mixture was stirred and mixed at a liquid temperature being held at about 20° C., to thereby obtain an aqueous mixed liquid B-1.
The aqueous mixed liquid A-1 was cooled at 70° C., and 58.60 kg of a silica sol containing 34.0% by mass in terms of $SiO_2$ was thereafter added. Then, 8.49 kg of a hydrogen peroxide solution containing 30% by mass of $H_2O_2$ was added, and stirred and mixed at 50° C. for 1 hour; and the aqueous mixed liquid B-1 was then added.
A liquid in which 13.8 kg of a fumed silica was dispersed in 186.8 kg of water, and 1.472 kg of bismuth nitrate $[Bi(NO_3)_2.6H_2O]$ were further sequentially added, and stirred at 50° C. for 2.5 hours to thereby obtain a raw material mixture.
In order to carry out a step of "preparation of a dried catalyst precursor" and a "calcination" step as described later in a continuous system, the present step was repeated 450 times to thereby prepare about 35 ton of the total of the raw material mixture.
(Preparation of a Dried Catalyst Precursor)
The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)
The calcination was carried out as in Example 1, except for the condition shown in Table 1, to obtain a catalyst.
(Evaluation of the Catalyst Performance)
The evaluation was carried out as in Example 1. The results are shown in Table 2.

Example 15

A silica-supported catalyst whose composition formula was represented by $Mo_1V_{0.24}Nb_{0.095}Sb_{0.27}Yb_{0.008}/45$ mass %-$SiO_2$ was produced as follows.
(Preparation of a Raw Material Mixture)
33.4 kg of ammonium heptamolybdate $[(NH_4)_6Mo_7O_{24}.4H_2O]$, 5.28 kg of ammonium metavanadate $[NH_4VO_3]$, 7.44 kg of diantimony trioxide $[Sb_2O_3]$, and 0.649 kg of ytterbium nitrate $[Yb(NO_3)_3.4H_2O]$ were added to 190.2 kg of water, and heated under stirring at 95° C. for 1 hour to thereby obtain an aqueous mixed liquid A-1.
4.05 kg of a hydrogen peroxide solution containing 30% by mass of $H_2O_2$ was added to 30.2 kg of the niobium raw material liquid. The mixture was stirred and mixed at a liquid temperature being held at about 20° C., to thereby obtain an aqueous mixed liquid B-1.
The aqueous mixed liquid A-1 was cooled at 70° C., and 58.60 kg of a silica sol containing 34.0% by mass in terms of $SiO_2$ was thereafter added. Then, 8.64 kg of a hydrogen peroxide solution containing 30% by mass of $H_2O_2$ was added, and stirred and mixed at 50° C. for 1 hour; and the aqueous mixed liquid B-1 was then added. A liquid in which 13.8 kg of a fumed silica was dispersed in 186.8 kg of water was further added, and stirred at 50° C. for 2.5 hours to thereby obtain a raw material mixture.
In order to carry out a step of "preparation of a dried catalyst precursor" and a "calcination" step as described later in a continuous system, the present step was repeated 450 times to thereby prepare about 35 ton of the total of the raw material mixture.
(Preparation of a Dried Catalyst Precursor)
The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)
The calcination was carried out as in Example 1, except for the condition shown in Table 1, to obtain a catalyst.
(Evaluation of the Catalyst Performance)
The evaluation was carried out as in Example 1. The results are shown in Table 2.

Example 16

A silica-supported catalyst whose composition formula was represented by $Mo_1V_{0.26}Nb_{0.095}Sb_{0.24}/45$ mass %-$SiO_2$ was produced as follows.
(Preparation of a Raw Material Mixture)
34.1 kg of ammonium heptamolybdate $[(NH_4)_6Mo_7O_{24}.4H_2O]$, 5.83 kg of ammonium metavanadate $[NH_4VO_3]$, and 6.74 kg of diantimony trioxide $[Sb_2O_3]$ were added to 21.0 kg of water, and heated under stirring at 95° C. for 1 hour to thereby obtain an aqueous mixed liquid A-1.
4.13 kg of a hydrogen peroxide solution containing 30% by mass of $H_2O_2$ was added to 30.8 kg of the niobium raw material liquid. The mixture was stirred and mixed at a liquid temperature being held at about 20° C., to thereby obtain an aqueous mixed liquid B-1.
The aqueous mixed liquid A-1 was cooled at 70° C., and 58.60 kg of a silica sol containing 34.0% by mass in terms of $SiO_2$ was thereafter added. Then, 7.82 kg of a hydrogen peroxide solution containing 30% by mass of $H_2O_2$ was added, and stirred and mixed at 50° C. for 1 hour; and the aqueous mixed liquid B-1 was then added. A liquid in which 13.8 kg of a fumed silica was dispersed in 186.8 kg of water was further added, and stirred at 50° C. for 2.5 hours to thereby obtain a raw material mixture.
In order to carry out a step of "preparation of a dried catalyst precursor" and a "calcination" step as described later in a continuous system, the present step was repeated 450 times to thereby prepare about 35 ton of the total of the raw material mixture.
(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)

The calcination was carried out as in Example 1, except for the condition shown in Table 1, to obtain a catalyst.
(Evaluation of the Catalyst Performance)

The evaluation was carried out as in Example 1. The results are shown in Table 2.

Example 17

A silica-supported catalyst whose composition formula was represented by $Mo_1V_{0.24}Nb_{0.095}Sb_{0.27}/45$ mass %-$SiO_2$ was produced as follows.
(Preparation of a Raw Material Mixture)

30.6 kg of ammonium heptamolybdate [$(NH_4)_6Mo_7O_{24}\cdot4H_2O$], 4.84 kg of ammonium metavanadate [$NH_4VO_3$], and 6.81 kg of diantimony trioxide [$Sb_2O_3$] were added to 174.1 kg of water, and heated under stirring at 95° C. for 1 hour to thereby obtain an aqueous mixed liquid A-1.

3.71 kg of a hydrogen peroxide solution containing 30% by mass of $H_2O_2$ was added to 27.6 kg of the niobium raw material liquid. The mixture was stirred and mixed at a liquid temperature being held at about 20° C., to thereby obtain an aqueous mixed liquid B-1.

The aqueous mixed liquid A-1 was cooled at 70° C., and 60.7 kg of a silica sol containing 34.0% by mass in terms of $SiO_2$ was thereafter added. Then, 7.91 kg of a hydrogen peroxide solution containing 30% by mass of $H_2O_2$ was added, and stirred and mixed at 50° C. for 1 hour; and the aqueous mixed liquid B-1 was then added. A liquid in which 16.9 kg of a fumed silica was dispersed in 236.3 kg of water was further added, and stirred at 50° C. for 2.5 hours to thereby obtain a raw material mixture.

In order to carry out a step of "preparation of a dried catalyst precursor" and a "calcination" step as described later in a continuous system, the present step was repeated 450 times to thereby prepare about 35 ton of the total of the raw material mixture.
(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)

The calcination was carried out as in Example 1, except for the condition shown in Table 1, to obtain a catalyst.
(Evaluation of the Catalyst Performance)

The evaluation was carried out as in Example 1. The results are shown in Table 2.

Example 18

A silica-supported catalyst whose composition formula was represented by $Mo_1V_{0.24}Nb_{0.095}Sb_{0.27}W_{0.031}Ce_{0.005}O_n/45$ mass %-$SiO_2$ was produced as follows.

(Preparation of a Raw Material Mixture)
A raw material mixture was prepared as in Example 1, except for preparing about 230 kg of the total of the raw material mixture by repeating three times the present step in order to carry out a step of "preparation of a dried catalyst precursor" and a "calcination" step in a continuous system.
(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.
(Calcination)

The same calcination apparatus as in Example 1 was used, except that the calcination apparatus had: a calcination tube 1 described below; a pair of hoods 2 (which were each of a cylindrical type opening at one terminal, and composed of a material of SUS, and had a size of a length of 100 mm for the powder inlet side and a length of 240 mm for the powder outlet side, and both had an internal diameter of 120 mm) respectively covering the open ends of the calcination tube 1; and a pair of V rings 3 (which were each of a V-shape having separated cross-sectional shapes (see FIG. 3(F)), and composed of a material of Viton rubber, and each had a size of an inner diameter of 92 mm, a width w of 40 mm, a height d2 of 7 mm and a wall thickness d1 of 3 mm, into each sealed chamber of which a nitrogen gas was introduced (the flow volume was 0.6 NL/min at each of the powder inlet side and the powder outlet side), and each had a sealing support whose size was a width of 45 mm, a width of a protrusion of 9 mm and a height (excluding the protrusion) of 30 mm, and whose material was SUS) respectively sealing gaps between the calcination tube 1 and the hoods 2. The dried catalyst precursor obtained was circulated at a rate of 70 g/hr and pre-stage-calcined in the SUS cylindrical calcination tube 1 which had an inner diameter of 80 mm, a length of 1,300 mm and a wall thickness of 3 mm, which was installed with seven weir plates having a height of 15 mm so that the length of a section of a heating furnace was divided into eight equal sections, and in which while a nitrogen gas was supplied at 1.3 NL/min from the powder inlet side, and a nitrogen gas was supplied at 0.7 NL/min from the powder outlet side, the temperature of the heating furnace was regulated so as to have a temperature profile of being raised up to 370° C. over about 5 hours and held at 370° C. for 3 hours in the state of the calcination tube 1 being rotated at 4 rpm, to thereby obtain a pre-stage calcination powder.

Then, the pre-stage calcination powder was circulated at a rate of 70 g/hr in the calcination apparatus using another SUS calcination tube 1 which had an inner diameter of 80 mm, a length of 1,300 mm and a wall thickness of 3 mm, which was installed with seven weir plates having a height of 18 mm so that the length of a section of a heating furnace was divided into eight equal sections, and which was being rotated at 4 rpm. At this time, while a portion which was a portion not being covered with the heating furnace of the powder inlet side of the calcination tube was hammered once at every 5 sec from a height of 15 mm above the calcination tube 1 in the direction perpendicular to the rotation axis by a hammering device equipped with a hammer of 2 kg in mass with a SUS hammering tip end, and while a nitrogen gas was being supplied at 0.9 NL/min from each of the powder inlet side and the powder outlet side, the temperature of the heating furnace was regulated so as to have a temperature profile of being raised up to 675° C. at 2° C./min, held at 675° C. for 2 hours for calcination, and descended at 1° C./min, to thereby carry out a main calcination of the pre-stage calcination powder to thereby obtain an oxide catalyst. During the main calcination, no decrease in the calcination temperature occurred and the oxide catalyst could be obtained at a stable rate. The vibration acceleration was measured by a vibrometer (MD-220, made by Asahi Kasei Technosystem Co., Ltd.), and was 70 m/s$^2$ and f was 1.85. The conditions of pressure, oxygen concentrations and the like in the specific space at this time were as shown in Table 2 for both the pre-stage calcination and the main calcination.

(Evaluation of the Catalyst Performance)

45 g of the oxide catalyst obtained after 48 hours from the calcination start was packed in a Vicol-glass fluidized-bed reaction tube having an inner diameter of 25 mm; and a mixed gas of propane:ammonia:oxygen:helium=1:0.85:3.0:11 in molar ratio was passed therethrough at a contact time of 3.0 (sec·g/cc) at a reaction temperature of 440° C. and under normal pressure of the reaction pressure. The reaction results after 2 days and 40 days from the start of the continuous calcination are shown in Table 2.

Example 19

A silica-supported catalyst whose composition formula was represented by $Mo_1V_{0.24}Nb_{0.095}Sb_{0.27}W_{0.031}Ce_{0.005}O_n$/45 mass %-$SiO_2$ was produced as follows.

(Preparation of a Raw Material Mixture)

A raw material mixture was prepared as in Example 1, except for preparing about 1 ton of the total of the raw material mixture by repeating 13 times the present step in order to carry out a step of "preparation of a dried catalyst precursor" and a "calcination" step in a continuous system.

(Preparation of a Dried Catalyst Precursor)

The raw material mixture obtained was fed and dried in a centrifugal-type spray dryer to thereby continuously obtain a fine spherical dried catalyst precursor. The inlet temperature of the dryer was 210° C.; and the outlet temperature was 120° C.

(Calcination)

The same calcination apparatus as in Example 1 was used, except that the calcination apparatus had: a calcination tube 1 described below; a pair of hoods 2 (which were each of a cylindrical type opening at one terminal, and composed of a material of SUS, and had a of a length of 65 mm for the powder inlet side and a length of 150 mm for the powder outlet side, and both had an internal diameter of 450 mm) respectively covering the open ends of the calcination tube 1; and a pair of V rings 3 (which were each of a V-shape having separated cross-sectional shapes (see FIG. 3(F)), and composed of a material of Viton rubber, and each had a size of an inner diameter of 380 mm, a width w of 40 mm, a height d2 of 7 mm and a wall thickness d1 of 3 mm, into each sealed chamber of which a nitrogen gas was introduced (the flow volume was 1.0 NL/min at each of the powder inlet side and the powder outlet side), and each had a sealing support whose size was a width of 45 mm, a width of a protrusion of 9 mm and a height (excluding the protrusion) of 45 mm, and whose material was SUS) respectively sealing gaps between the calcination tube 1 and the hoods 2. The dried catalyst precursor obtained was circulated at a rate of 85 g/hr and pre-stage-calcined in the SUS cylindrical calcination tube 1 which had an inner diameter of 300 mm, a length of 800 mm and a wall thickness of 7 mm, which was installed with five weir plates having a height of 60 mm so that the length of a section of a heating furnace was divided into six equal sections, and in which while a nitrogen gas was circulated at 1.5 NL/min from the powder inlet side, and a nitrogen gas was circulated at 1 NL/min from the powder outlet side, the temperature of the heating furnace was regulated so as to have a temperature profile of being raised up to 370° C. over about 5 hours and held at 370° C. for 3 hours in the state of the calcination tube being rotated at 4 rpm, to thereby obtain a pre-stage calcination powder.

Then, the pre-stage calcination powder was circulated at a rate of 85 g/hr in the calcination apparatus using another SUS calcination tube 1 which had an inner diameter of 300 mm, a length of 800 mm and a wall thickness of 7 mm, which was installed with five weir plates having a height of 75 mm so that the length of a section of a heating furnace was divided into six equal sections, and which was being rotated at 4 rpm. At this time, while a portion which was a portion not being covered with the heating furnace of the powder inlet side of the calcination tube was hammered once at every 5 sec from a height of 30 mm above the calcination tube 1 in the direction perpendicular to the rotation axis by a hammering device equipped with a hammer of 8 kg in mass with a SUS hammering tip end, and while a nitrogen gas was being supplied at 1.1 NL/min from each of the powder inlet side and the powder outlet side, the temperature of the heating furnace was regulated so as to have a temperature profile of being raised up to 675° C. at 2° C./min, held at 675° C. for 2 hours for calcination, and descended at 1° C./min, to thereby carry out a main calcination of the pre-stage calcination powder to thereby obtain an oxide catalyst. During the main calcination, no decrease in the calcination temperature occurred and the oxide catalyst could be obtained at a stable rate. The vibration acceleration was measured by a vibrometer (MD-220, made by Asahi Kasei Technosystem Co., Ltd.), and was 50 m/s$^2$ and f was 2.53. The conditions of pressure, oxygen concentrations and the like in the specific space at this time were as shown in Table 2 for both the pre-stage calcination and the main calcination.

(Evaluation of the Catalyst Performance)

45 g of the oxide catalyst obtained after 48 hours from the calcination start was packed in a Vicol-glass fluidized-bed reaction tube having an inner diameter of 25 mm; and a mixed gas of propane:ammonia:oxygen:helium=1:0.85:3.0:11 in molar ratio was passed therethrough at a contact time of 3.0 (sec·g/cc) at a reaction temperature of 440° C. and under normal pressure of the reaction pressure. The reaction results after 2 days and 40 days from the start of the continuous calcination are shown in Table 2.

Example 20

A silica-supported catalyst whose composition formula was represented by $Mo_1V_{0.24}Nb_{0.095}Sb_{0.27}W_{0.031}Ce_{0.005}O_n$/45 mass %-$SiO_2$ was produced as in Example 1, except for making the vibration acceleration during the main calcination to be 2 m/s$^2$ and f to be 0.07, and altering the impartation of an impact to once at every 30 sec; and the catalyst performance was evaluated as in Example 1. The results are shown in Table 2.

Example 21

A silica-supported catalyst whose composition formula was represented by $Mo_1V_{0.24}Nb_{0.095}Sb_{0.27}W_{0.031}Ce_{0.005}O_n$/45 mass %-$SiO_2$ was produced as in Example 1, except for making the vibration acceleration during the main calcination to be 1,400 m/s$^2$ and f to be 53.4, and altering the impartation of an impact to once at every 30 sec; and the catalyst performance was evaluated as in Example 1. The results are shown in Table 2.

Example 22

In order to prepare a silica-supported catalyst whose composition formula was represented by $Mo_1V_{0.24}Nb_{0.095}Sb_{0.27}W_{0.031}Ce_{0.005}O_n$/45 mass %-$SiO_2$, a dried catalyst precursor was prepared as in Example 1, and the pre-stage calcination was carried out as in Example 1, except for making the vibration acceleration during the pre-stage calcination to be 55 m/s$^2$ and f to be 2.08. The reduction index (RI) of the pre-stage calcination powder obtained is shown in Table 3.

Example 23

The pre-stage calcination was carried out as in Example 22, except for no impartation of an impact during the pre-stage calcination. The reduction index (RI) of the pre-stage calcination powder obtained is shown in Table 3.

TABLE 1

| | Ring (Seal) Structure | Pressure in Specific Space P1 (mmH$_2$O) | Pressure Difference from Sealed Chamber P2 (mmH$_2$O) | Oxygen Concentration Before Calcination Start (ppm) | Oxygen Concentration After 15 Days (ppm) | Oxygen Concentration After 40 Days (ppm) |
|---|---|---|---|---|---|---|
| Example 1 | V RING | 50 | 55 | 10 | 11 | 11 |
| Example 2 | V RING | 100 | 30 | 12 | 12 | 13 |
| Example 3 | V RING | 0 | 60 | 28 | 30 | 35 |
| Example 4 | V RING | 0 | 40 | 90 | 100 | 200 |
| Example 5 | V RING | 0 | 0 | 140 | 180 | 250 |
| Example 6 | Lip seal | 50 | 40 | 30 | 34 | 40 |
| Example 7 | Lip seal | 40 | 20 | 35 | 41 | 50 |
| Comparative Example 1 | O RING | 50 | — | 1300 | 1800 | 3000 |
| Comparative Example 2 | Oil seal | 0 | — | 700 | 850 | 1200 |
| Comparative Example 3 | Oil seal | 50 | — | 200 | 390 | 1050 |
| Comparative Example 4 | Oil seal | 100 | — | 60 | 1000 | — |

| | Vibration Acceleration (m/sec$^2$) | f | Impact Frequency | Hammer Weight (kg) | Hammer Height (mm) | Yield on 2 Days after Continuous Calcination (%) | Yield on 15 Days after Continuous Calcination (%) | Yield on 40 Days after Continuous Calcination (%) |
|---|---|---|---|---|---|---|---|---|
| Example 1 | 55 | 2.08 | once at every 5 sec | 16 | 250 | 53.3 | — | 53.4 |
| Example 2 | 60 | 2.27 | once at every 7 sec | 3 | 35 | 53.2 | — | 53.1 |
| Example 3 | 55 | 2.08 | once at every 10 sec | 16 | 250 | 52.5 | — | 52.3 |
| Example 4 | 55 | 2.08 | once at every 15 sec | 16 | 250 | 52.1 | — | 51.3 |
| Example 5 | 55 | 2.08 | once at every 10 sec | 16 | 240 | 52.1 | — | 50.9 |
| Example 6 | 60 | 2.27 | once at every 7 sec | 3 | 35 | 52.8 | 52.6 | 52.2 |
| Example 7 | 55 | 2.08 | once at every 5 sec | 16 | 250 | 52.7 | — | 51.9 |
| Comparative Example 1 | 60 | 2.27 | once at every 7 sec | 3 | 35 | 50.3 | 45.1 | 39.2 |
| Comparative Example 2 | 55 | 2.08 | once at every 5 sec | 16 | 250 | 50.5 | — | 43.8 |
| Comparative Example 3 | 55 | 2.08 | once at every 5 sec | 16 | 250 | 51.0 | 49.9 | 44.0 |
| Comparative Example 4 | 55 | 2.08 | once at every 7 sec | 3 | 35 | 52.8 | 44.1 | — |

TABLE 2

| | Ring (Seal) Structure | Pressure in Specific Space P1 (mmH$_2$O) | Pressure Difference from Sealed Chamber P2 (mmH$_2$O) | Oxygen Concentration Before Calcination Start (ppm) | Oxygen Concentration (m/s$^2$) |
|---|---|---|---|---|---|
| Example 8 | V RING | 50 | 55 | 10 | 55 |
| Example 9 | V RING | 50 | 55 | 10 | 82 |
| Example 10 | V RING | 50 | 55 | 10 | 53 |

TABLE 2-continued

| | | Pressure in Specific Space P1 (mmH₂O) | Pressure Difference from Sealed Chamber P2 (mmH₂O) | Oxygen Concentration (ppm) | |
|---|---|---|---|---|---|
| Example 11 | V RING | 50 | 55 | 10 | 50 |
| Example 12 | V RING | 50 | 55 | 10 | 45 |
| Example 13 | V RING | 50 | 55 | 10 | 62 |
| Example 14 | V RING | 50 | 55 | 10 | 65 |
| Example 15 | V RING | 50 | 55 | 10 | 54 |
| Example 16 | V RING | 50 | 55 | 10 | 46 |
| Example 17 | V RING | 50 | 55 | 10 | 48 |
| Example 18 | V RING | 50 | 55 | 10 | 70 |
| Example 19 | V RING | 50 | 55 | 10 | 50 |
| Example 20 | V RING | 50 | 55 | 10 | 2 |
| Example 21 | V RING | 50 | 55 | 10 | 1400 |

| | f | Impact Frequency | Hammer Weight (kg) | Hammer Height (mm) | Yield on 2 Days after Continuous Calcination (%) | Yield on 40 Days after Continuous Calcination (%) |
|---|---|---|---|---|---|---|
| Example 8 | 2.08 | once at every 5 sec | 16 | 250 | 52.8 | 52.8 |
| Example 9 | 3.10 | once at every 5 sec | 22 | 260 | 53.1 | 53 |
| Example 10 | 2.00 | once at every 5 sec | 22 | 250 | 52.3 | 52.2 |
| Example 11 | 1.89 | once at every 5 sec | 22 | 200 | 52.0 | 51.9 |
| Example 12 | 1.70 | once at every 5 sec | 12 | 250 | 52.8 | 52.8 |
| Example 13 | 2.34 | once at every 5 sec | 18 | 250 | 51.9 | 51.9 |
| Example 14 | 2.46 | once at every 5 sec | 18 | 260 | 52.9 | 53.0 |
| Example 15 | 2.04 | once at every 5 sec | 18 | 260 | 52.4 | 52.4 |
| Example 16 | 1.74 | once at every 5 sec | 12 | 250 | 49.5 | 49.4 |
| Example 17 | 1.81 | once at every 5 sec | 13 | 250 | 53.2 | 53.2 |
| Example 18 | 2.64 | once at every 5 sec | 2 | 15 | 52.7 | 52.8 |
| Example 19 | 1.89 | once at every 5 sec | 8 | 50 | 52.9 | 52.8 |
| Example 20 | 0.07 | once at every 5 sec | 0.25 | 100 | 52.4 | 49.2 |
| Example 21 | 53.4 | once at every 30 sec | 70 | 1500 | 52.5 | 51.9 |

TABLE 3

| | Ring (Seal) Structure | Pressure in Specific Space P1 (mmH₂O) | Pressure Difference from Sealed Chamber P2 (mmH₂O) | Oxygen Concentration (ppm) |
|---|---|---|---|---|
| Example 22 | V RING | 50 | 55 | 10 |
| Example 23 | V RING | 50 | 55 | 10 |

| | Vibration Acceleration (m/sec²) | f | Impact Frequency | Hammer Weight (kg) | Hammer Height (mm) | RI (%) |
|---|---|---|---|---|---|---|
| Example 22 | 55 | 2.08 | once at every 10 sec | 14 | 250 | 10.09 |
| Example 23 | 0 | 0 | — | — | — | 10.07 |

The present application is based on Japanese Patent Application (Japanese Patent Laid-Open No. 2011-033777), filed on Feb. 18, 2011, the disclosure of which is incorporated herein by reference in its entirety.

INDUSTRIAL APPLICABILITY

The present invention can provide a calcination apparatus of which the atmosphere in a calcination tube can be maintained even in a long-term operation, a method for continuously producing a catalyst which provides a target product in a high yield, and a method for producing an unsaturated acid or an unsaturated nitrile using the catalyst obtained by the production method. Therefore, the present invention has industrial applicability as an apparatus or the like for producing a catalyst used in a method for producing an unsaturated acid or an unsaturated nitrile.

DESCRIPTION OF SYMBOLS

1 ... CALCINATION TUBE, 2 ... HOOD, 3 ... RING, 20, 21 ... INERT GAS INLET, 30 ... GROOVE, and 300 ... SEALED CHAMBER

The invention claimed is:

1. A calcination apparatus, comprising:
a calcination tube having open ends at both terminals;
a pair of hoods, each hood covering each open end of the calcination tube; and
a pair of rings, each ring sealing a gap between the calcination tube and the hood,
wherein the rings are directly or indirectly fixed on an outer surface of the calcination tube;
a groove is provided along a circumferential direction of the ring at a contact surface side between the ring and the hood;
a sealed chamber surrounded by the hood and the groove is formed; a pair of flanges, each flange protruding from an inner surface of the hood toward an inside in a circumferential direction of the calcination tube,
wherein each of the plurality of annular members is in contact with each of the pair of flanges; and
both the calcination tube and the rings rotate in a circumferential direction of the calcination tube while keeping the hood in contact with both sides of the groove.

2. A calcination apparatus, comprising:
a calcination tube having open ends at both terminals;
a pair of hoods, each hood covering each open end of the calcination tube; and
a pair of rings, each ring sealing a gap between the calcination tube and the hood,
wherein the rings are directly or indirectly fixed on an outer surface of the calcination tube;
each of the rings comprises a plurality of annular members disposed in a width direction of the ring;
each of the plurality of annular members comes into contact with the hood;
a sealed chamber surrounded by at least the hood and the plurality of annular members is formed; a pair of flanges, each flange protruding from an inner surface of the hood toward an inside in a circumferential direction of the calcination tube, wherein each of the plurality of annular members is in contact with each of the pair of flanges and
both the calcination tube and the rings rotate in a circumferential direction of the calcination tube while keeping the hood in contact with the plurality of annular members.

3. The calcination apparatus according to claim 1, wherein a space surrounded by at least the calcination tube, the rings, and the hood is maintained under an inert gas atmosphere; and the sealed chamber is filled with an inert gas.

4. The calcination apparatus according to claim 3, wherein the hood comprises a supply port for supplying the inert gas to the sealed chamber.

5. The calcination apparatus according to claim 3, wherein an atmospheric pressure within the space is higher than an atmospheric pressure outside the space.

6. The calcination apparatus according to claim 3, wherein a pressure difference P1 represented by the following equation (1) is more than 0 mm $H_2O$ and 900 mm $H_2O$ or less:

$P1$=(an atmospheric pressure within the space)−(an atmospheric pressure outside the space)　　(1).

7. The calcination apparatus according to claim 3, wherein a pressure difference P2 represented by the following equation (2) is more than 0 mm $H_2O$ and 500 mm $H_2O$ or less:

$P2$=(a pressure of the sealed chamber)−(a pressure within the space)　　(2).

8. The calcination apparatus according to claim 3, wherein an oxygen concentration of the space is 1000 ppm or less.

9. The calcination apparatus according to claim 1, further comprising a unit for imparting an impact to the calcination tube.

10. The calcination apparatus according to claim 2, wherein a space surrounded by at least the calcination tube, the rings, and the hood is maintained under an inert gas atmosphere; and the sealed chamber is filled with an inert gas.

11. The calcination apparatus according to claim 10, wherein the hood comprises a supply port for supplying the inert gas to the sealed chamber.

12. The calcination apparatus according to claim 10, wherein an atmospheric pressure within the space is higher than an atmospheric pressure outside the space.

13. The calcination apparatus according to claim 10, wherein a pressure difference P1 represented by the following equation (1) is more than 0 mm $H_2O$ and 900 mm $H_2O$ or less:

$P1$=(an atmospheric pressure within the space)−(an atmospheric pressure outside the space)　　(1).

14. The calcination apparatus according to claim 10, wherein a pressure difference P2 represented by the following equation (2) is more than 0 mm $H_2O$ and 500 mm $H_2O$ or less:

$P2$=(a pressure of the sealed chamber)−(a pressure within the space)　　(2).

15. The calcination apparatus according to claim 10, wherein an oxygen concentration of the space is 1000 ppm or less.

16. The calcination apparatus according to claim 10, further comprising a unit for imparting an impact to the calcination tube.

* * * * *